United States Patent
Xu et al.

(10) Patent No.: US 11,384,384 B1
(45) Date of Patent: Jul. 12, 2022

(54) METHODS AND REAGENT KITS FOR BISULFITE CONVERSION OF DNA

(71) Applicant: URIT Medical Electronic Co., Ltd., Guilin (CN)

(72) Inventors: Tom Cheng Xu, Castro Valley, CA (US); Kuikui Shen, Guilin (CN); Sally Li Shen, Castro Valley, CA (US); Jinlan Xu, Guilin (CN); Shilei Tang, Guilin (CN); Jusong Liang, Guilin (CN)

(73) Assignee: URIT Medical Electronic Co., Ltd.

( * ) Notice: Subject to any disclaimer, the term of this patent is extended or adjusted under 35 U.S.C. 154(b) by 0 days.

(21) Appl. No.: 17/659,472

(22) Filed: Apr. 15, 2022

Related U.S. Application Data

(62) Division of application No. 17/452,648, filed on Oct. 28, 2021, now Pat. No. 11,332,777.

(51) Int. Cl.
  *C12Q 1/6806* (2018.01)
  *C12Q 1/6858* (2018.01)
  *B01L 7/00* (2006.01)

(52) U.S. Cl.
  CPC ............ *C12Q 1/6806* (2013.01); *B01L 7/525* (2013.01); *C12Q 1/6858* (2013.01); *B01L 2400/0409* (2013.01); *B01L 2400/0487* (2013.01)

(58) Field of Classification Search
  CPC ...... C12Q 1/6806; C12Q 1/6858; B01L 7/525
  See application file for complete search history.

(56) References Cited

U.S. PATENT DOCUMENTS

| | | |
|---|---|---|
| 10,533,210 B2 | 1/2020 | Nauwelaers et al. |
| 10,731,215 B2* | 8/2020 | Ballhause ............ C12Q 1/6806 |
| 2013/0164826 A1 | 6/2013 | Zhou |

OTHER PUBLICATIONS

Tetzner et al., "Control of carry-over contamination for PCR-based DNA methylation quantification using bisulfite treated DNA," Nucleic Acids Research, vol. 35, No. 1, e4, pp. 1-7. (Year: 2007).*

Colell et al., "Novel roles for GAPDH in cell death and carcinogenesis", Cell Death and Differentiation, (2009) 16, 1573-1581.

(Continued)

*Primary Examiner* — Young J Kim
(74) *Attorney, Agent, or Firm* — Levine Bagade Han LLP

(57) ABSTRACT

Disclosed herein are methods, reagent kits, and compositions for performing a bisulfite conversion of DNA directly from a biological sample including a patient's urine sample or a slide-mounted FFPE tissue sample. For example, a method of performing a bisulfite conversion of DNA can comprise certain preliminary steps for processing the biological sample and transferring a portion of the processed sample into a reaction vessel containing a bisulfite mixture. The method can further comprise heating the reaction vessel containing the biological sample and the bisulfite mixture at several heating temperatures and subsequently holding the reaction vessel at a holding temperature for a holding period. The method can also comprise certain bisulfite removal steps, desulfonation steps, and removal of the desulfonation solution. A final elution step can yield the converted DNA for further downstream sequencing and analysis.

10 Claims, 10 Drawing Sheets

(56) References Cited

OTHER PUBLICATIONS

Frommer, Marianne, et al. "A genomic sequencing protocol that yields a positive display of 5-methylcytosine residues in individual DNA strands." Proceedings of the National Academy of Sciences (1992) 89.5: 1827-1831).
Kandyala, R., et al., "Xylene: An overview of its health hazards and preventive measures," Journal of Oral and Maxillofacial Pathology, 14(1):1-5, 2010.
Ren et al. "Methylation analysis of SHOX2 and RASSF1A in bronchoalveolar lavage fluid for early lung cancer diagnosis." Ann Diagn Pathol 27 (2017).
Shi et al. "Performance Evaluation of SHOX2 and RASSF1A Methylation for the Aid in Diagnosis of Lung Cancer Based on the Analysis of FFPE Specimen." Frontiers in Oncology 10 (2020): 2768.
Zhang et al. "DNA methylation analysis of the SHOX2 and RASSF1A panel in bronchoalveolar lavage fluid for lung cancer diagnosis." Journal of Cancer 8.17 (2017): 3585.

* cited by examiner

| Sample | Conversion Kit and Method | DNA Concentration using Fluorometer (ng/μL) | SYBR Green qPCR (Ct) | A260/A280 |
|---|---|---|---|---|
| Direct conversion of FFPE of human lung tissue showing signs of non-small cell lung cancer | EpiMark® bisulfite conversion kit and associated protocol | 1.34 | 32.09 | 1.64 |
| | | 1.37 | 32.01 | 1.79 |
| | BisulFlash® DNA modification kit and associated protocol | 0.83 | 26.71 | 2.13 |
| | | 0.95 | 27.58 | 1.78 |
| | Presently disclosed kit and method | 1.33 | 24.77 | 2.46 |
| | | 0.83 | 25.17 | 2.30 |

FIG. 6A

| Sample | Conversion Kit and Method | DNA Concentration using Fluorometer (ng/μL) | SYBR Green qPCR (Ct) | A260/A280 |
|---|---|---|---|---|
| Direct conversion of human urine sample | EpiMark® bisulfite conversion kit and associated protocol | 0.20 | 28.29 | 1.60 |
| | | 0.13 | 32.80 | 1.46 |
| | BisulFlash® DNA modification kit and associated protocol | 0.14 | 26.13 | 1.49 |
| | | 0.11 | 26.58 | 1.51 |
| | Presently disclosed kit and method | 0.11 | 24.34 | 2.39 |
| | | 0.15 | 25.08 | 2.04 |

FIG. 6B

| Sample | Conversion Kit and Method | DNA Concentration using Fluorometer (ng/μL) | SYBR Green qPCR (Ct) |
|---|---|---|---|
| cfDNA (Patient 1) | EpiMark® bisulfite conversion kit and associated protocol | 0.3 | 35.19 |
| | Presently disclosed kit and method | 0.3 | 32.53 |
| cfDNA (Patient 2) | EpiMark® bisulfite conversion kit and associated protocol | 0.2 | 36.21 |
| | Presently disclosed kit and method | 0.2 | 32.70 |

FIG. 6C

| Sample | Sample Type/ Conversion Status | DNA Concentration using Fluorometer (ng/μL) | SYBR Green qPCR using primers designed for unconverted DNA (Ct) | SYBR Green qPCR using primers designed for converted DNA (Ct) |
|---|---|---|---|---|
| Purified human genomic DNA (Patient 1) | DNA prior to conversion | 2.54 | 24.97 | 40.00 |
| Purified human genomic DNA (Patient 1) | Bisulfite Converted DNA | 0.36 | 40.00 | 23.59 |
| Purified human genomic DNA (Patient 2) | DNA prior to conversion | 3.52 | 24.92 | 40.00 |
| Purified human genomic DNA (Patient 2) | Bisulfite Converted DNA | 0.29 | 40.00 | 24.83 |

FIG. 7

METHODS AND REAGENT KITS FOR BISULFITE CONVERSION OF DNA

CROSS-REFERENCE TO RELATED APPLICATION

This application is a divisional of U.S. patent application Ser. No. 17/452,648 filed on Oct. 28, 2021, the content of which is incorporated herein by reference in its entirety.

TECHNICAL FIELD

The present disclosure relates generally to the field of deoxyribonucleic acid (DNA) methylation detection and, more specifically, to methods and reagent kits for bisulfite conversion of DNA from urine and formalin-fixed paraffin-embedded (FFPE) tissue samples.

BACKGROUND

The biological significance of DNA methylation in the regulation of gene expression and its role in tumorigenesis is of keen interest for researchers and clinicians. Alterations in the methylation status of genomic DNA can result in transcriptional silencing of such important regulators as tumor suppressor genes. In higher-order eukaryotes, DNA is most often methylated at cytosines located 5' to guanosine at sequence strands enriched in cytosine-guanosine dinucleotides (CpGs or so called "CpG islands"). The methylation process occurs by covalent addition of a methyl group that converts the cytosine to 5-methylcytosine.

The two established approaches for detecting whether such methylation has occurred involve methylation-specific digestion enzymes and selective chemical conversion of unmethylated cytosines to uracil using bisulfite followed by methylation-specific polymerase chain reaction (PCR). Since the former can only be used on a select number of sequences containing restriction sites that are recognizable by the digestion enzymes, bisulfite conversion is the more widely-used of the two approaches.

Bisulfite conversion refers to a reaction whereby unmethylated cytosine bases in nucleic acid are converted to uracil bases in the presence of bisulfite ions without significant conversion of 5-methylcytosines. Traditionally, a bisulfite conversion reaction involves a deamination step involving incubating the DNA with a bisulfite solution, removal of the bisulfite by desalting, a desulfonation step, and removal of the desulfonation solution (see Frommer, Marianne, et al. "A genomic sequencing protocol that yields a positive display of 5-methylcytosine residues in individual DNA strands." *Proceedings of the National Academy of Sciences* (1992) 89.5: 1827-1831).

Most bisulfite conversion protocols require the use of isolated or purified DNA as the starting material. However, the process of isolating or purifying a patient's DNA from tissue samples such as FFPE tissue samples or bodily fluids such as urine can result in significant loss of DNA even before the bisulfite conversion protocol is initiated. This is problematic when it comes to pathological diagnostics where critical patient tissue samples (e.g., from biopsies) are often in short supply. Moreover, although some bisulfite conversion kits now purport to offer direct DNA modification from whole cells or bodily fluids, the protocols for such kits still require that multiple reagents or buffers be added to the cell samples or bodily fluids before the conversion process can begin.

Specifically, when it comes to FFPE samples, the few bisulfite conversion protocols that can use such samples all require that the FFPE slides be deparaffinized in an aromatic solvent such as xylene. However, the health hazards of xylene are well documented and those with long-term exposure to xylene can develop headaches, dizziness, nausea, and vomiting (see Kandyala, R., Raghavendra, S. P. C., & Rajasekharan, S. T. Xylene: An overview of its health hazards and preventive measures. *Journal of Oral and Maxillofacial Pathology* (2010) 14(1): 1-5).

Furthermore, a major drawback of all previous bisulfite conversion protocols is that conversion reaction times often range between several hours to several days depending on the conversion kit used. Even conversion kits considered "rapid" still often require at least 120 minutes for the initial incubation or deamination step. These long reaction times are needed to ensure adequate conversion and to exclude false-positive results. However, such long reaction times can lead to degradation of the DNA starting material and inadvertent deamination of methylcytosine to thymine.

Therefore, a solution is needed which reduces the long reaction times of previous bisulfite conversion protocols and kits yet maintains or improves the quantity and quality of converted sequence yields compared to such previous protocols and kits. Such a solution should also allow patient tissue samples such as FFPE samples or bodily fluids to be used directly as the starting material. Moreover, such a solution should be cost-effective compared to conventional bisulfite conversion kits and should lessen the risk of clinician or operator error by reducing the number of steps needed to undertake the protocol.

SUMMARY

Disclosed herein are methods and reagent kits for performing a bisulfite conversion of DNA directly from a patient's urine sample or FFPE tissue sample. The methods and reagent kits disclosed herein can also be used to perform a bisulfite conversion of DNA using isolated or purified DNA.

For example, a method of performing a bisulfite conversion of DNA from a urine sample as part of a DNA-methylation-based urinalysis is disclosed. The method can comprise introducing an aliquot of the urine sample into a first reaction vessel (e.g., a microcentrifuge tube or a well of a multi-well plate). The urine sample can be a direct urine sample without any buffers added to the urine sample. The method can further comprise centrifuging the urine sample within the first reaction vessel and removing at least part of a supernatant from the first reaction vessel by decanting or pipetting the supernatant out of the first reaction vessel. The urine-derived cellular debris from the urine sample remains at the bottom of the first reaction vessel after at least part of the supernatant is removed.

The method can also comprise re-suspending the urine-derived cellular debris within the first reaction vessel by vortexing or shaking the first reaction vessel and transferring a portion of the re-suspended urine-derived cellular debris from the first reaction vessel into a second reaction vessel containing a bisulfite mixture.

In some embodiments, the bisulfite mixture can comprise ammonium bisulfite, ammonium sulfite, sodium bisulfite, and deionized water.

In certain embodiments, a volume ratio of the re-suspended urine-derived cellular debris transferred to the bisulfite mixture within the second reaction vessel is between 1:6 to 1:7 (e.g., 1:6.5).

The method can further comprise heating the second reaction vessel containing the urine-derived cellular debris and the bisulfite mixture using a heating apparatus at a first heating temperature between 93° C. and 98° C. (for example, between 94° C. and 96° C., or, as a more specific example, 95° C.) for a first heating period between 4 minutes and 6 minutes (for example, for 5 minutes), immediately lowering a temperature of the heating apparatus after the first heating period to a second heating temperature between 88° C. and 92° C. (for example, between 89° C. and 91° C., or, as a more specific example, 90° C.) for a second heating period between 8 minutes and 12 minutes (for example, between 9 minutes and 11 minutes, or, as a more specific example, 10 minutes), and then holding the second reaction vessel at a holding temperature between 58° C. and 62° C. (for example, at 60° C.) for a holding period between 30 seconds and 90 seconds (for example, for 60 seconds) to produce a modified sample. In some embodiments, the same heating apparatus can be used to heat the second reaction vessel containing the urine-derived cellular debris and the bisulfite mixture at the first heating temperature for the first heating period, at the second heating temperature for the second heating period, and at the holding temperature for the holding period.

The method can further comprise immediately removing the second reaction vessel containing the modified sample from the heating apparatus upon completion of the holding period and centrifuging the second reaction vessel. The second reaction vessel is centrifuged without any further heating of the second reaction vessel beyond the heating period.

In some embodiments, the bisulfite mixture within the second reaction vessel can be a frozen bisulfite mixture. A temperature of the frozen bisulfite mixture can be between 0° C. and −25° C. In these embodiments, the portion of the re-suspended urine-derived cellular debris can be introduced directly into the second reaction vessel comprising the frozen bisulfite mixture.

In other embodiments, the bisulfite mixture within the second reaction vessel can be a partially frozen bisulfite mixture. In these embodiments, the portion of the re-suspended urine-derived cellular debris can be introduced directly into the second reaction vessel comprising the partially frozen bisulfite mixture.

The method can also comprise introducing the modified sample from the second reaction vessel into a third reaction vessel (e.g., another microcentrifuge tube) containing a binding buffer to produce a binding buffer-and-modified sample solution. The method can further comprise closing a lid of the third reaction vessel and inverting the third reaction vessel at least ten times and transferring the binding buffer-and-modified sample solution to a mini adsorption column positioned within a first collection tube. The method can also comprise centrifuging the first collection tube containing the mini adsorption column and discarding a filtrate collected within the first collection tube and placing the mini adsorption column back into the first collection tube.

In some embodiments, the binding buffer can be a guanidine hydrochloride solution having a concentration of between 5 M and 6 M.

The method can also comprise adding a wash buffer solution to the mini adsorption column, centrifuging the first collection tube containing the mini adsorption column, discarding the filtrate collected within the first collection tube, and placing the mini adsorption column back into the first collection tube. The method can further comprise adding a desulphonation mixture to the mini adsorption column within the first collection tube and allowing the mini adsorption column to remain undisturbed at a temperature between 18° C. and 28° C. for between 10 minutes and 20 minutes.

The method can further comprise centrifuging the first collection tube containing the mini adsorption column, discarding the filtrate collected within the first collection tube, and placing the mini adsorption column back into the first collection tube. The method can also comprise adding additional instances of the wash buffer solution to the mini adsorption column, centrifuging the first collection tube containing the mini adsorption column, discarding the filtrate collected within the first collection tube, and placing the mini adsorption column back into the first collection tube. The method can further comprise adding further instances of the wash buffer solution to the mini adsorption column, centrifuging the first collection tube containing the mini adsorption column, and discarding the filtrate collected within the first collection tube.

In some embodiments, the desulphonation mixture can comprise sodium hydroxide in 90% (v/v) ethanol. The concentration of the sodium hydroxide within the mixture can be between 0.2 M and 0.4 M.

The method can further comprise placing the mini adsorption column into a second collection tube and allowing the mini adsorption column to dry at a temperature between 18° C. and 28° C. for between 1 minute and 5 minutes. The method can also comprise adding an elution buffer to a center of the mini adsorption column within the second collection tube and allowing the mini adsorption column to remain at a temperature between 18° C. and 28° C. for between 1 minute and 5 minutes. The method can further comprise centrifuging the second collection tube containing the mini adsorption column and discarding the mini adsorption column. The filtrate collected within the second collection tube comprises bisulfite converted DNA for further DNA methylation analysis.

In alternative embodiments, the method can also comprise introducing the modified sample from the second reaction vessel into a third reaction vessel containing a binding buffer and a carboxylated paramagnetic bead solution and centrifuging the third reaction vessel. The method can also comprise placing the third reaction vessel in proximity to a magnet for between 3 minutes and 8 minutes and removing and discarding a supernatant formed within the third reaction vessel. The method can further comprise adding a wash buffer solution to the third reaction vessel and vortexing and centrifuging the third reaction vessel. The method can further comprise placing the third reaction vessel in proximity to the magnet for between 1 minute and 3 minutes and removing and discarding a supernatant formed within the third reaction vessel.

The method can also comprise adding a desulphonation mixture to the third reaction vessel and allowing the third reaction vessel to remain at a temperature between 18° C. and 28° C. for a period of time between 10 minutes and 20 minutes. The third reaction vessel can be inverted at least two times during this period of time with a lid of the third reaction vessel closed. The method can also comprise centrifuging the third reaction vessel, placing the third reaction vessel in proximity to the magnet for between 1 minute and 3 minutes, and removing and discarding a supernatant formed within the third reaction vessel.

The method can further comprise adding additional instances of the wash buffer solution to the third reaction vessel and vortexing and centrifuging the third reaction vessel. The method can further comprise placing the third reaction vessel in proximity to the magnet for between 1 minute and 3 minutes and removing and discarding a supernatant formed within the third reaction vessel. The method can also comprise adding an elution buffer to the third reaction vessel and allowing the third reaction vessel to remain at a temperature between 18° C. and 28° C. for between 3 minutes and 8 minutes. The method can further comprise centrifuging the third reaction vessel and placing the third reaction vessel in proximity to the magnet for between 1 minute and 3 minutes. A supernatant formed within the third reaction vessel can comprise bisulfite converted DNA for further DNA methylation analysis.

Also disclosed is a method of performing a bisulfite conversion of DNA from a FFPE tissue sample as part of a DNA-methylation-based tissue analysis. The method can comprise introducing a piece of the FFPE tissue sample into a first reaction vessel (e.g., a microcentrifuge tube or a well of a multi-well plate) and adding a nucleic acid buffer to the first reaction vessel to produce a buffered sample. The method can also comprise heating the buffered sample at between 70° C. and 98° C. for between 8 minutes and 12 minutes while mixing the buffered sample using a thermomixer or mixing the buffered sample via intermittent shaking. The method can further comprise adding a digestion enzyme mixture to the buffered sample when the temperature of the buffered sample is below 50° C. to produce an enzyme-and-sample mixture. In some embodiments, a volume ratio of the nucleic acid buffer added to the digestion enzyme mixture added is 100:1.

The method can also comprise vortexing and centrifuging the enzyme-and-sample mixture and subsequently heating the enzyme-and-sample mixture at between 50° C. and 65° C. for between 25 minutes and 35 minutes while mixing the enzyme-and-sample mixture using a thermomixer or mixing the enzyme-and-sample mixture via intermittent shaking. The method can also comprise further heating the enzyme-and-sample mixture at between 85° C. and 95° C. for between 30 seconds and 90 seconds and allowing the temperature of the enzyme-and-sample mixture to equilibrate to between 18° C. and 28° C.

The method can further comprise vortexing and centrifuging the enzyme-and-sample mixture at between 15,000×g to 17,000×g for between 30 seconds and 90 seconds and transferring a supernatant from the first reaction vessel (the digested FFPE solution) into a second reaction vessel containing a bisulfite mixture.

In certain embodiments, the bisulfite mixture can comprise ammonium bisulfite, ammonium sulfite, sodium bisulfite, and deionized water.

The method can further comprise heating the second reaction vessel containing the digested FFPE solution and the bisulfite mixture using a heating apparatus at a first heating temperature between 93° C. and 98° C. (for example, between 94° C. and 96° C., or, as a more specific example, 95° C.) for a first heating period between 4 minutes and 6 minutes (for example, for 5 minutes), immediately lowering a temperature of the heating apparatus after the first heating period to a second heating temperature between 88° C. and 92° C. (for example, between 89° C. and 91° C., or, as a more specific example, 90° C.) for a second heating period between 8 minutes and 12 minutes (for example, between 9 minutes and 11 minutes, or, as a more specific example, 10 minutes), and then holding the second reaction vessel at a holding temperature between 58° C. and 62° C. (for example, at 60° C.) for a holding period between 30 seconds and 90 seconds (for example, for 60 seconds) to produce a modified sample.

In some embodiments, the same heating apparatus can be used to heat the second reaction vessel containing the digested FFPE solution and the bisulfite mixture at the first heating temperature for the first heating period, at the second heating temperature for the second heating period, and at the holding temperature for the holding period.

The method can also comprise immediately removing the second reaction vessel containing the modified sample from the heating apparatus upon completion of the holding period and centrifuging the second reaction vessel. The second reaction vessel is centrifuged without any further heating of the reaction vessel beyond the heating period.

In some embodiments, the bisulfite mixture within the second reaction vessel can be a frozen bisulfite mixture. For example, the temperature of the frozen bisulfite mixture can be between 0° C. and −25° C. In these embodiments, the digested FFPE solution can be introduced directly into the second reaction vessel including the frozen bisulfite mixture.

In other embodiments, the bisulfite mixture within the second reaction vessel can be a partially frozen bisulfite mixture. In these embodiments, the digested FFPE solution can be introduced directly into the second reaction vessel including the partially frozen bisulfite mixture.

The method can further comprise introducing the modified sample from the second reaction vessel into a third reaction vessel containing a binding buffer to produce a binding buffer-and-modified sample solution.

In some embodiments, the binding buffer can be a guanidine hydrochloride solution having a concentration of between 5 M and 6 M.

The method can also comprise closing a lid of the third reaction vessel and inverting the third reaction vessel at least ten times. The method can further comprise transferring the binding buffer-and-modified sample solution to a mini adsorption column positioned within a first collection tube. The method can also comprise centrifuging the first collection tube containing the mini adsorption column, discarding a filtrate collected within the first collection tube, and placing the mini adsorption column back into the first collection tube.

The method can further comprise adding a wash buffer solution to the mini adsorption column and centrifuging the first collection tube containing the mini adsorption column and discarding the filtrate collected within the first collection tube and placing the mini adsorption column back into the first collection tube.

The method can also comprise adding a desulphonation mixture to the mini adsorption column within the first collection tube and allowing the mini adsorption column to remain undisturbed at a temperature between 18° C. and 28° C. for between 10 minutes and 20 minutes.

In some embodiments, the desulphonation mixture can comprise sodium hydroxide in 90% (v/v) ethanol. For example, a concentration of the sodium hydroxide is between 0.2 M and 0.4 M.

The method can further comprise centrifuging the first collection tube containing the mini adsorption column and discarding the filtrate collected within the first collection tube and placing the mini adsorption column back into the first collection tube.

The method can also comprise adding additional instances of the wash buffer solution to the mini adsorption column, centrifuging the first collection tube containing the mini adsorption column, discarding the filtrate collected within the first collection tube, and placing the mini adsorption column back into the first collection tube. The method can also comprise adding additional instances of the wash buffer solution to the mini adsorption column, centrifuging the first collection tube containing the mini adsorption column, and discarding the filtrate collected within the first collection tube.

The method can also comprise placing the mini adsorption column into a second collection tube and allowing the mini adsorption column to dry at a temperature between 18° C. and 28° C. for between 1 minute and 5 minutes. The method can also comprise adding an elution buffer to a center of the mini adsorption column within the second collection tube and allowing the mini adsorption column to remain at a temperature between 18° C. and 28° C. for between 1 minute and 5 minutes. The method can further comprise centrifuging the second collection tube containing the mini adsorption column and discarding the mini adsorption column. The filtrate collected within the second collection tube comprises bisulfite converted DNA for further DNA methylation analysis.

In alternative embodiments, the method can also comprise introducing the modified sample from the second reaction vessel into a third reaction vessel containing a binding buffer and a carboxylated paramagnetic bead solution and centrifuging the third reaction vessel. The method can also comprise placing the third reaction vessel in proximity to a magnet for between 3 minutes and 8 minutes and removing and discarding a supernatant formed within the third reaction vessel. The method can further comprise adding a wash buffer solution to the third reaction vessel and vortexing and centrifuging the third reaction vessel. The method can further comprise placing the third reaction vessel in proximity to the magnet for between 1 minute and 3 minutes and removing and discarding a supernatant formed within the third reaction vessel.

The method can also comprise adding a desulphonation mixture to the third reaction vessel and allowing the third reaction vessel to remain at a temperature between 18° C. and 28° C. for a period of time between 10 minutes and 20 minutes. The third reaction vessel can be inverted at least two times during this period of time with a lid of the third reaction vessel closed. The method can also comprise centrifuging the third reaction vessel, placing the third reaction vessel in proximity to the magnet for between 1 minute and 3 minutes, and removing and discarding a supernatant formed within the third reaction vessel.

The method can further comprise adding additional instances of the wash buffer solution to the third reaction vessel and vortexing and centrifuging the third reaction vessel. The method can further comprise placing the third reaction vessel in proximity to the magnet for between 1 minute and 3 minutes and removing and discarding a supernatant formed within the third reaction vessel. The method can also comprise adding an elution buffer to the third reaction vessel and allowing the third reaction vessel to remain at a temperature between 18° C. and 28° C. for between 3 minutes and 8 minutes. The method can further comprise centrifuging the third reaction vessel and placing the third reaction vessel in proximity to the magnet for between 1 minute and 3 minutes. A supernatant formed within the third reaction vessel can comprise bisulfite converted DNA for further DNA methylation analysis.

Disclosed herein is also a bisulfite conversion kit or a reagent kit for performing bisulfite conversion of DNA for downstream DNA methylation analysis. The kit can comprise a bisulfite mixture, a binding buffer, a wash buffer solution, a desulphonation mixture, and an elution buffer.

In some embodiments, the kit can also comprise a nucleic acid buffer and a digestion enzyme mixture. In certain embodiments, the bisulfite mixture can comprise ammonium bisulfite, ammonium sulfite, sodium bisulfite, and deionized water. The bisulfite mixture can be pre-aliquoted into reaction vessels or tubes and the reaction vessels or tubes containing the pre-aliquoted bisulfite mixture can be frozen.

The binding buffer can be a guanidine hydrochloride solution. The wash buffer solution can be a solution of tris(hydroxymethyl)aminomethane (Tris)-hydrochloric acid (HCl) in 80% (v/v) ethanol. The wash buffer solution can have a pH of about 7.0. The desulphonation mixture can be a solution comprising NaOH in 90% (v/v) ethanol. The elution buffer can be a 1× Tris-ethylenediaminetetraacetic acid (Tris-EDTA or TE) buffer.

Moreover, the nucleic acid buffer can comprise a Tris-HCl solution, sodium chloride (NaCl), EDTA, and sodium dodecyl sulphate (SDS). The digestion enzyme mixture can be a solution comprising proteinase K.

BRIEF DESCRIPTION OF THE DRAWINGS

FIG. 6A is a table comparing the performance of the presently disclosed bisulfite conversion kit and method with two conventional bisulfite conversion kits and their associated protocols as it relates to the quantity and purity of the converted DNA.

FIG. 6B is another table comparing the performance of the presently disclosed bisulfite conversion kit and method with the same two conventional bisulfite conversion kits and their associated protocols as it relates to the quantity and purity of the converted DNA.

FIG. 6C is yet another table comparing the performance of the presently disclosed bisulfite conversion kit and method with the same two conventional bisulfite conversion kits and their associated protocols as it relates to the quantity and purity of the converted DNA.

FIG. 7 is a table showing the results of methylation assays conducted using SYBR Green qPCR with the GAPDH gene as the target sequence.

DETAILED DESCRIPTION

Disclosed herein are methods, reagent kits, and compositions for performing a bisulfite conversion of DNA directly from a patient's urine sample or a slide-mounted FFPE tissue sample. In some embodiments, the methods, reagent kits, and compositions disclosed herein can also be used to perform a bisulfite conversion of DNA from isolated/purified genomic DNA or cell-free DNA (cfDNA).

Figure 1:
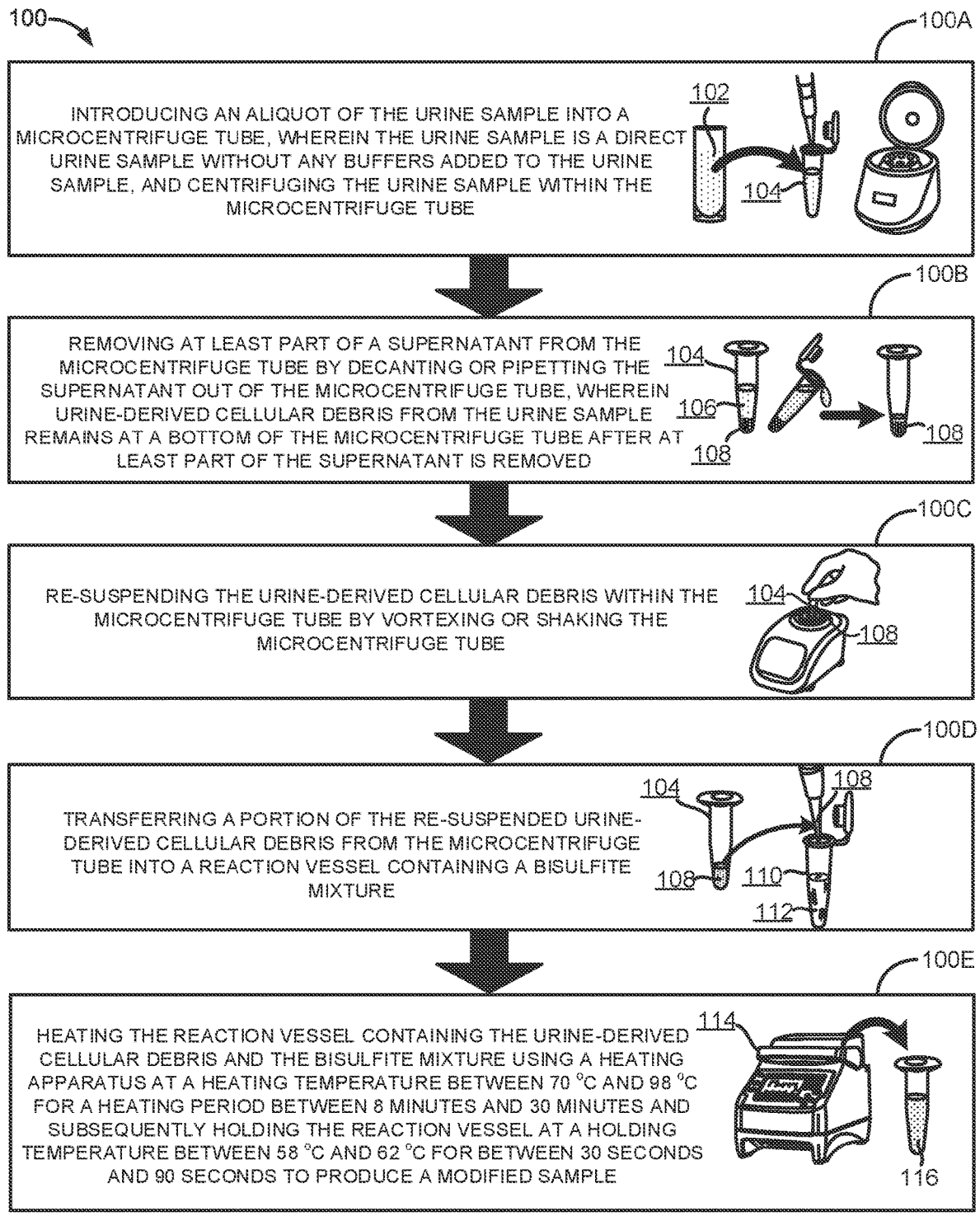
FIG. 1 illustrates one embodiment of a method of performing a bisulfite conversion of DNA from a urine sample.

FIG. 1 illustrates one embodiment of a method 100 of performing a bisulfite conversion of DNA from a urine sample. The method 100 can be part of a DNA-methylation-based urinalysis conducted as part of a screening test or disease diagnostic panel. For example, the method 100 can be the first steps in a DNA methylation detection protocol for detection of bladder cancer and/or prostate cancer.

The method 100 can comprise introducing an aliquot of a urine sample 102 into a first reaction vessel such as a microcentrifuge tube 104 or another type of collection tube (e.g., a PCR tube) compatible with a benchtop laboratory centrifuge in step 100A. The aliquot can be between 8 mL and 12 mL (e.g., 10 mL).

The urine sample 102 can be a direct urine sample collected from a patient without any buffers added to the urine sample subsequent to the sample collection. The urine sample 102 can be a sample collected via a catheter or a clean catch urine sample.

In some embodiments, the urine sample 102 can be refrigerated or kept on ice before introducing the aliquot of the urine sample 102 into the microcentrifuge tube 104. For example, the temperature of the urine sample 102 can be between 2° C. to 40° C. when the aliquot of the urine sample 102 is introduced into the microcentrifuge tube 104.

One unexpected discovery made by the applicant is that the bisulfite conversion method 100 disclosed herein can use a direct urine sample obtained from a patient as the starting material without any buffers or buffering solutions added to the urine sample. The converted sequence yields obtained from such a direct urine sample are nearly equivalent to the quantity and quality of the converted sequence yields obtained from a processed urine sample or a urine sample with buffers added to the sample. This reduces the cost and components of a reagent kit (for example, the reagent kit disclosed herein) for performing a bisulfite conversion of DNA from a urine sample.

It is contemplated by this disclosure (and it should be understood by one of ordinary skill in the art) that, in alternative embodiments, one or more buffers or buffering solutions can be added to the urine sample 102 prior to introducing the aliquot of the urine sample 102 into the microcentrifuge tube 104.

Step 100A can also comprise centrifuging the urine sample 102 within the microcentrifuge tube 104. In some embodiments, the urine sample 102 can be centrifuged at a relative centrifugal force of between 1500×g and 2000×g for between 8 minutes and 12 minutes. For example, the urine sample 102 can be centrifuged at about 1800×g for approximately 10 minutes. In some embodiments, the centrifuge can have a rotor radius of about 10.0 cm.

The method 100 can also comprise removing at least part of a supernatant 106 from the microcentrifuge tube 104 by decanting or pipetting most of the supernatant 106 out of the microcentrifuge tube 104 in step 100B. A urine-derived cellular debris 108 from the urine sample 102 is what remains at the bottom of the microcentrifuge tube 104 after most of the supernatant 106 is removed. For example, between 80 μL and 120 μL (e.g., about 100 μL) of the urine-derived cellular debris 108 (along with some remaining supernatant 106) can remain at the bottom of the microcentrifuge tube 104 after most of the supernatant 106 is removed from the microcentrifuge tube 104.

The method 100 can further comprise re-suspending the urine-derived cellular debris 108 within the microcentrifuge tube 104 by vortexing or shaking the microcentrifuge tube 104 in step 100C. The microcentrifuge tube 104 can be vortexed using a benchtop vortex mixer or shaker. The microcentrifuge tube 104 containing the urine-derived cellular debris 108 can be vortexed between 30 seconds and 60 seconds (e.g., 45 seconds).

The method 100 can also comprise transferring a portion of the re-suspended urine-derived cellular debris 108 from the microcentrifuge tube 104 into another reaction vessel 110 containing a bisulfite mixture 112 in step 100D.

In some embodiments, the reaction vessel 110 is a reaction tube (e.g., a PCR tube) or a well of a multi-well plate pre-filled and pre-aliquoted with the bisulfite mixture 112. Transferring the portion of the re-suspended urine-derived cellular debris 108 into the reaction vessel 110 can comprise pipetting an aliquot of the re-suspended urine-derived cellular debris 108 into the reaction vessel 110 containing the bisulfite mixture 112.

In one embodiment, the bisulfite mixture 112 within the reaction vessel 110 can be a frozen bisulfite mixture. For example, the temperature of the frozen bisulfite mixture can be between 0° C. and −25° C. In this embodiment, the aliquot of the re-suspended urine-derived cellular debris 108 can be introduced directly into the reaction vessel 110 comprising the frozen bisulfite mixture 112.

In another embodiment, the bisulfite mixture 112 within the reaction vessel 110 can be a partially frozen bisulfite mixture. For example, at least part of the bisulfite mixture can be frozen while the remainder of the bisulfite mixture can be thawed and in liquid form. In this embodiment, the aliquot of the re-suspended urine-derived cellular debris 108 can be introduced directly into the reaction vessel 110 comprising the partially frozen bisulfite mixture.

In some embodiments, a volume ratio of the re-suspended urine-derived cellular debris 108 transferred to the bisulfite mixture 112 within the reaction vessel 110 can be between 1:6 to 1:7. For example, the volume ratio of the re-suspended urine-derived cellular debris 108 transferred to the bisulfite mixture 112 within the reaction vessel 110 can be about 1:6.5. As a more specific example, about 20 μL of the re-suspended urine-derived cellular debris 108 can be added to about 130 μL of the bisulfite mixture 112 within the reaction vessel 110.

One unexpected discovery made by the applicant is that re-suspended urine-derived cellular debris 108 can be added directly to a frozen or partially frozen instance of the bisulfite mixture 112 disclosed herein without previously heating up the frozen or partially frozen bisulfite mixture 112 or allowing the frozen bisulfite mixture 112 to come to room temperature. The applicant discovered that the converted sequence yields obtained from a method where the re-suspended urine-derived cellular debris 108 was added directly to a frozen or partially frozen bisulfite mixture 112 were nearly equivalent to the quantity and quality of the converted sequence yields obtained from a method where the bisulfite mixture 112 was allowed to come to room temperature prior to adding the re-suspended urine-derived cellular debris 108. This means a reaction vessel 110 containing the pre-aliquoted bisulfite mixture 112 can be retrieved directly from a freezer and the re-suspended urine-derived cellular debris 108 can be added to the reaction vessel 110 without the lab technician or clinician having to set aside the bisulfite mixture 112 and keeping track of when the bisulfite mixture 112 was removed from the freezer. This cuts down the amount of time it takes to undertake the entire bisulfite conversion by at least 20 to 30 minutes. This time-saving step can greatly benefit clinical laboratories that process multiple urine samples a day.

Moreover, formulating bisulfite conversion reagents is normally a tedious and error-ridden process and the reagents must be used within a short period of time due to its instability. The present method and kits disclosed herein allows technicians or clinicians to undertake bisulfite conversion reactions without having to undertake this tedious formulation procedure. The pre-aliquoted bisulfite mixture 112 disclosed herein can be stored at between 0° C. and −25° C. and can be used immediately upon retrieval from a freezer or refrigerator. This nullifies any issues related to the instability of the reagents and saves the technician or clinician from having to repeatedly re-formulate such reagents to ensure their stability.

It is contemplated by this disclosure (and it should be understood by one of ordinary skill in the art) that, in alternative embodiments, the frozen or partially frozen bisulfite mixture 112 can be allowed to equilibrate or come to room temperature before the re-suspended urine-derived cellular debris 108 is added to the bisulfite mixture 112 within the reaction vessel 110.

The bisulfite mixture 112 can comprise ammonium bisulfite, ammonium sulfite, sodium bisulfite, and deionized water. Presented in Table 1 below is an example formulation for a 10 M bisulfite mixture 112:

TABLE 1

Example Composition of 10M Bisulfite Mixture

| Mixture Component | Amount (in grams) |
| --- | --- |
| 68% (w/w, aqueous) Ammonium Bisulfite | 5.1 g |
| Sodium Bisulfite | 2.1 g |
| Ammonium Sulfite | 0.7 g |
| Deionized $H_2O$ | 1.3 g |

The method can further comprise heating the reaction vessel 110 containing the urine-derived cellular debris 108 and the bisulfite mixture 112 using a heating apparatus 114 at a first heating temperature between 93° C. and 98° C. (for example, between 94° C. and 96° C., or, as a more specific example, 95° C.) for a first heating period between 4 minutes and 6 minutes (for example, for 5 minutes) and then immediately lowering a temperature of the heating apparatus 114 after the first heating period to a second heating temperature between 88° C. and 92° C. (for example, between 89° C. and 91° C., or, as a more specific example, 90° C.) for a second heating period between 8 minutes and 12 minutes (for example, between 9 minutes and 11 minutes, or, as a more specific example, 10 minutes) in step 100E. For example, the reaction vessel 110 containing the urine-derived cellular debris 108 and the bisulfite mixture 112 can be heated at 95° C. for 5 minutes and then the temperature can be lowered to 90° C. and the reaction vessel 110 containing the urine-derived cellular debris 108 can be heated for another 10 minutes at this new lowered heating temperature.

In some embodiments, the heating apparatus 114 can be a PCR thermal cycler. In other embodiments, the heating apparatus 114 can be a thermomixer. As a more specific example, the heating apparatus 114 can be an Eppendorf™ 5350 Thermomixer 5350 distributed by Eppendorf AG.

Step 100E can be preceded by a step where a lid of the reaction vessel 110 is closed and the reaction vessel 110 containing the urine-derived cellular debris 108 and the bisulfite mixture 112 is inverted several times and centrifuged briefly. For example, the reaction vessel 110 containing the urine-derived cellular debris 108 and the bisulfite mixture 112 can be inverted several times and immediately centrifuged at between about 10,000×g to about 12,000×g for approximately 30 seconds to 90 seconds.

Step 100E can further comprise subsequently holding the reaction vessel 110 at a holding temperature between 58° C. and 62° C. (for example, at 60° C.) for a holding period between 30 seconds and 90 seconds (for example, for 60 seconds) to produce a modified sample 116. In some embodiments, step 100E can comprise subsequently holding the reaction vessel 110 at a holding temperature of 60° C. for about 60 seconds.

It has been discovered by the applicants that this unique heating process, where the reaction vessel 110 containing the urine-derived cellular debris 108 and the bisulfite mixture 112 disclosed herein is heated at 95° C. for about 5 minutes, followed by heating at 90° C. for about 10 minutes, and then immediately lowering the temperature to 60° C. for about 1 minute is effective in obtaining converted DNA at concentrations (in ng/μL) substantially equivalent to and, in some cases, even higher than those produced by conventional bisulfite conversion kits in a fraction of the time. This was not expected as those of ordinary skill in the art would assume that heating the urine-derived cellular debris and the bisulfite mixture at such high temperatures for such a short amount of time would damage the DNA in the sample or would negatively affect the conversion reaction.

In some embodiments, the same heating apparatus 114 can be used to heat the reaction vessel 110 containing the urine-derived cellular debris 108 and the bisulfite mixture 112 at the first heating temperature for the first heating period, at the second heating temperature for the second heating period, and at the holding temperature for the holding period.

Step 100E can also comprise immediately removing the reaction vessel 110 containing the modified sample 116 from the heating apparatus 114 upon completion of the holding period and briefly centrifuging the reaction vessel 110. For example, the reaction vessel 110 containing the modified sample 116 can be removed from the heating apparatus 114 and immediately centrifuged at between about 10,000×g to about 12,000×g for approximately 30 seconds to 90 seconds. The reaction vessel 110 can be centrifuged without any further heating of the reaction vessel 110 beyond the heating period.

Figure 4A:
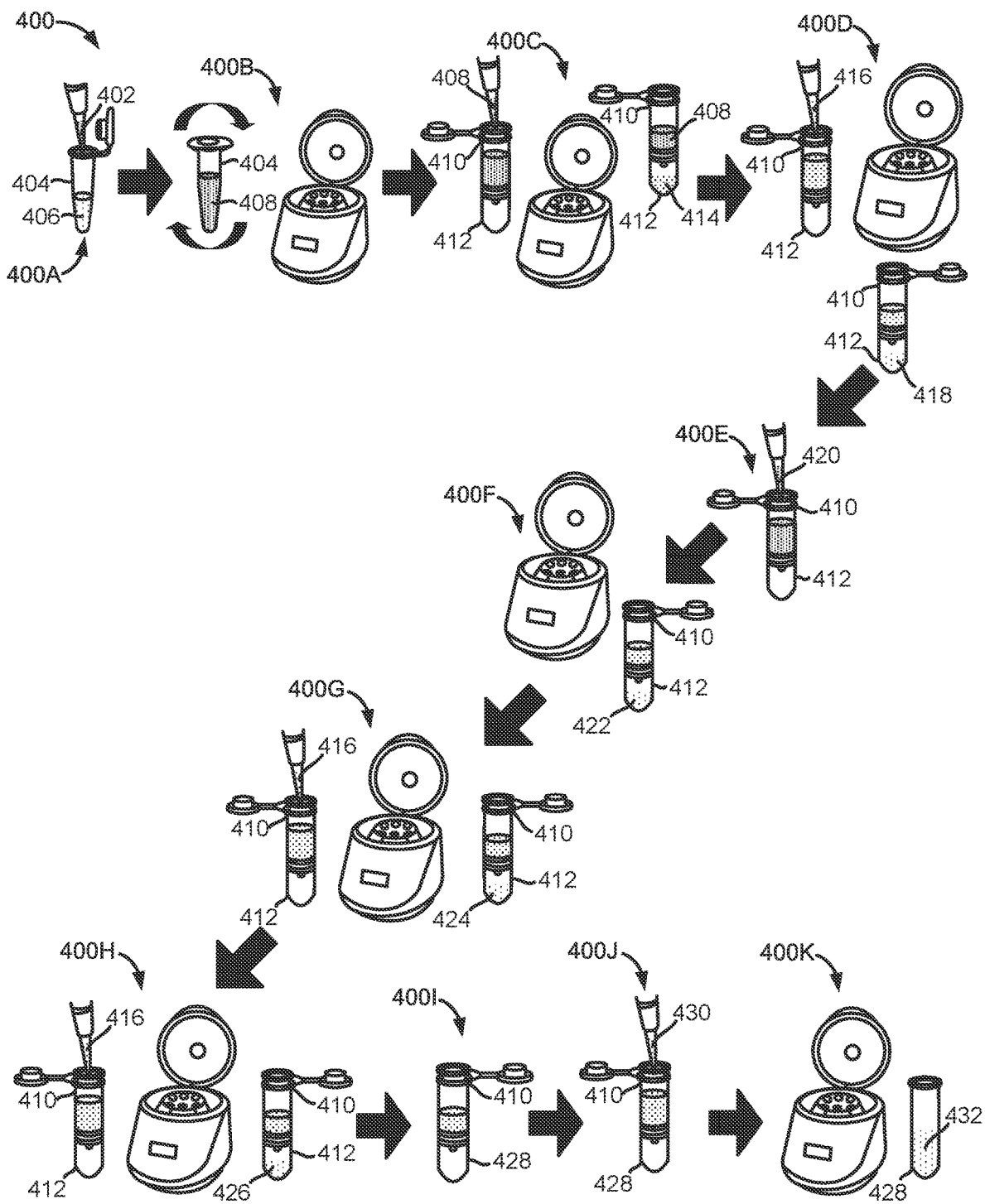
FIG. 4A illustrates additional method steps for processing a modified sample for producing converted DNA.
Figure 4B:
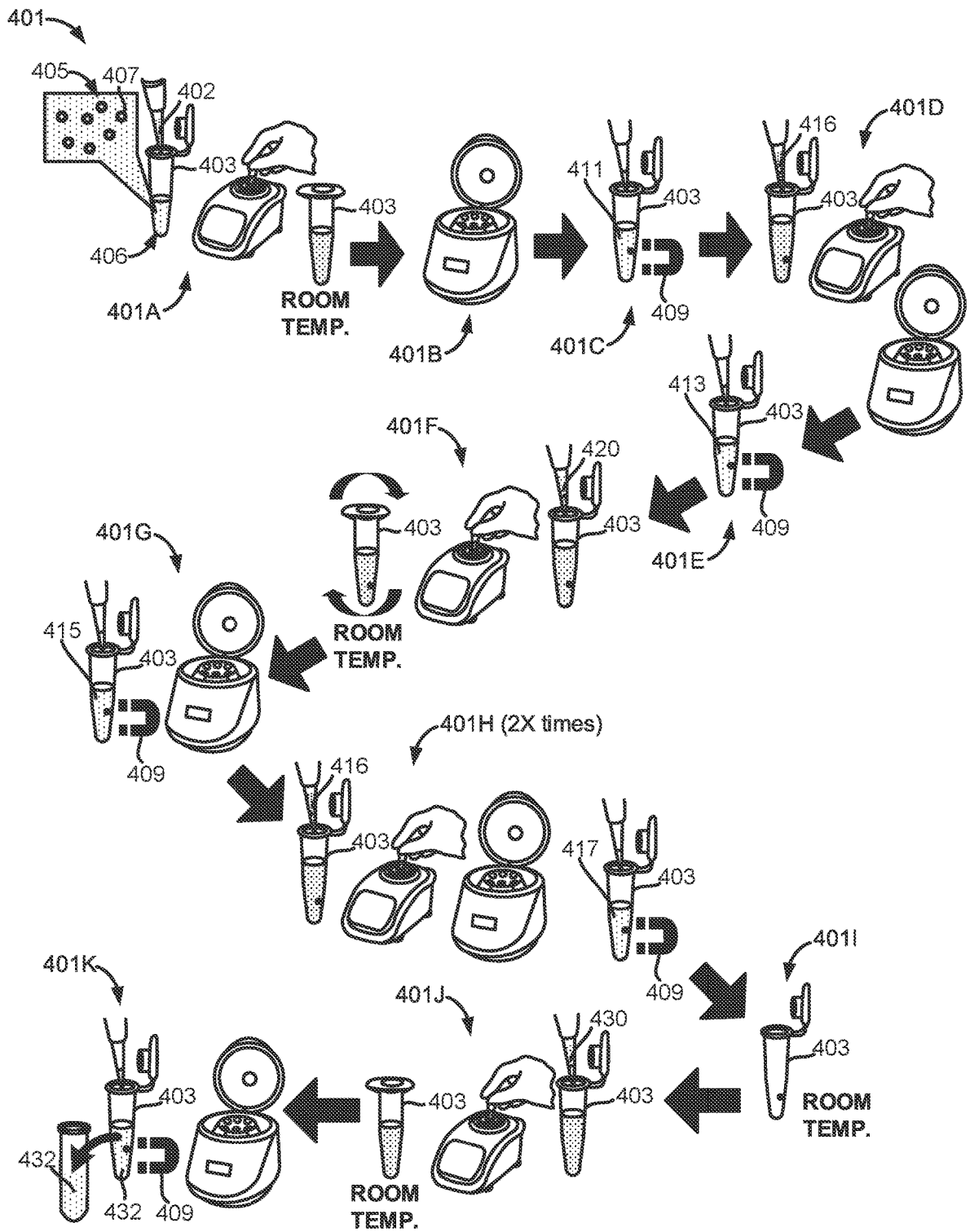
FIG. 4B illustrates an alternative set of additional method steps for processing a modified sample for producing converted DNA.

The modified sample 116 can then be subject to certain additional method steps 400, as depicted and described with respect to FIG. 4A, or, alternatively, additional method steps 401, as depicted and described with respect to FIG. 4B, to produce the converted DNA 432 for further downstream sequencing and analysis. The additional method steps 400 and steps 401 can comprise one or more bisulfite removal steps, desulfonation steps, and removal of the desulfonation solution. A final elution step can yield the converted DNA 432 for further downstream sequencing and analysis.

Figure 2:
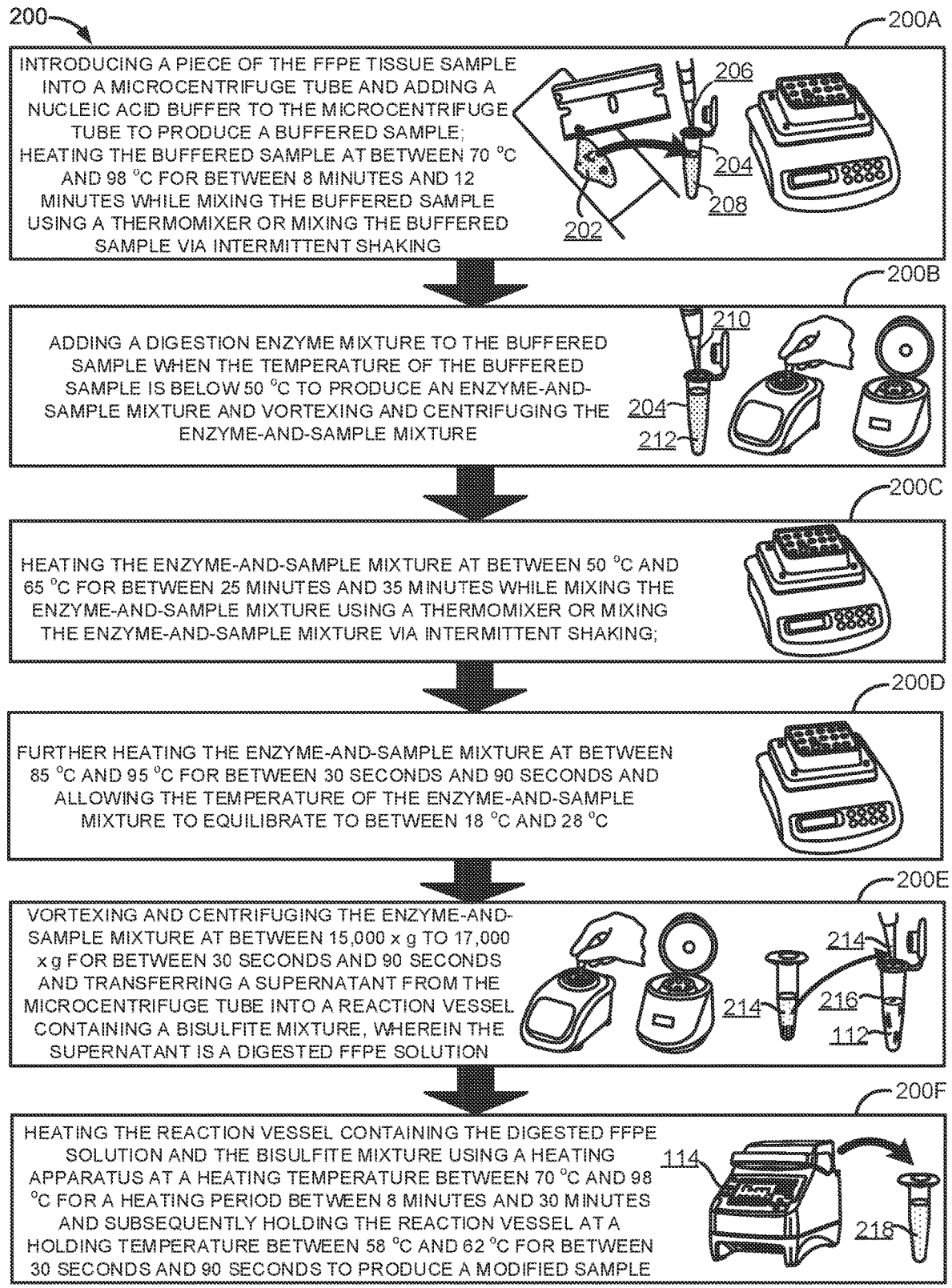
FIG. 2 illustrates one embodiment of a method of performing a bisulfite conversion of DNA from an FFPE tissue sample.

FIG. 2 illustrates one embodiment of a method 200 of performing a bisulfite conversion of DNA from an FFPE tissue sample. The method 200 can be part of a DNA-methylation-based tissue analysis conducted as part of a screening test or a disease diagnostic test/panel such as a biopsy.

The method 200 disclosed herein can be applied to a wide-array of FFPE tissue samples including bladder tissue samples, breast tissue samples, cervical tissue samples, colorectal tissue samples, esophageal tissues samples, gastric tissue samples, renal tissue samples, hepatic tissue samples, lung tissue samples, lymphoid tissue samples, skin tissue samples, nasopharyngeal tissue samples, ovarian tissue samples, prostate tissue samples, and thyroid tissue samples.

The method 200 can comprise introducing a piece of an FFPE tissue sample 202 into a first reaction vessel such as a microcentrifuge tube 204 and adding a nucleic acid buffer 206 to the microcentrifuge tube 204 to produce a buffered sample 208 in step 200A. For example, the FFPE tissue sample 202 can be scraped off (e.g., using a blade or scraper) of a glass slide serving as a carrier for the FFPE tissue sample 202.

In one embodiment, the microcentrifuge tube 204 can be a 1.5 mL microcentrifuge tube. In this embodiment, between about 3 mg and 10 mg of the FFPE tissue sample 202 can be introduced into the microcentrifuge tube 204 and between about 80 µL and 120 µL (e.g., about 100 µL) of the nucleic acid buffer 206 can be added to the microcentrifuge tube 204.

In some instances, the piece of the FFPE tissue sample 202 can be introduced into the microcentrifuge tube 204 and the microcentrifuge tube 204 can be centrifuged briefly to allow the FFPE tissue sample 202 to collect at the bottom of the microcentrifuge tube 204. For example, the microcentrifuge tube 204 containing the FFPE tissue sample 202 can be centrifuged at about 1800×g for approximately 5 minutes. This can be done before introducing the nucleic acid buffer 206 into the microcentrifuge tube 204.

The nucleic acid buffer 206 can comprise a Tris-hydrochloride (Tris-HCl) solution, sodium chloride (NaCl), ethylenediaminetetraacetic acid (EDTA), and sodium dodecyl sulfate (SDS). Presented in Table 2 below is an example formulation of the nucleic acid buffer 206:

TABLE 2

Example Composition of Nucleic Acid Buffer

| Buffer Component | Concentration |
| --- | --- |
| Tris-HCl (pH 7.5) | 100 mM |
| NaCl | 200 mM |
| EDTA | 2 mM |
| SDS | 1% |

Step 200A can further comprise heating the buffered sample 208 at between 70° C. and 98° C. for between 8 minutes and 12 minutes while mixing/shaking the buffered sample 208 using a thermomixer. When a thermomixer is not available, the buffered sample 208 can be heated at between 70° C. and 98° C. for between 8 minutes and 12 minutes and, during this period, the buffered sample 208 can be mixed or shaken by removing the microcentrifuge tube 204 from the heating apparatus intermittently and shaking the microcentrifuge tube 204.

The method 200 can also comprise removing the microcentrifuge tube 204 containing the buffered sample 208 from the thermomixer or other type of heating apparatus and allowing the buffered sample 208 to equilibrate to a temperature below 50° C. in step 200B. Step 200B can further comprise adding a digestion enzyme mixture 210 to the buffered sample 208 to produce an enzyme-and-sample mixture 212. For example, step 200B can comprise adding between 0.8 µL and 1.2 µL (e.g., about 1.0 µL) of the digestion enzyme mixture 210 to the buffered sample 208 to produce the enzyme-and-sample mixture 212.

In one embodiment, the digestion enzyme mixture 210 can be a solution comprising proteinase K. For example, the digestion enzyme mixture 210 can comprise approximately 20 mg/mL of proteinase K.

In certain embodiments, the volume ratio of the nucleic acid buffer 206 to the digestion enzyme mixture 210 within the enzyme-and-sample mixture 212 is between 95:1 to 105:1. For example, the volume ratio of the nucleic acid buffer 206 to the digestion enzyme mixture 210 within the enzyme-and-sample mixture 212 can be about 100:1.

Step 200B can also comprise vortexing the enzyme-and-sample mixture 212 for between 10 seconds and 20 seconds (e.g., about 15 seconds) and centrifuging the enzyme-and-sample mixture 212 briefly. The enzyme-and-sample mixture 212 can be centrifuged at between about 10,000×g to about 12,000×g for approximately 30 seconds to 90 seconds.

The method 200 can further comprise heating the enzyme-and-sample mixture 212 at between 50° C. and 65° C. for between 25 minutes and 35 minutes while mixing/shaking the enzyme-and-sample mixture 212 using a thermomixer in step 200C. For example, the enzyme-and-sample mixture 212 can be heated at about 56° C. for about 30 minutes while being shaken/mixed by the thermomixer.

When a thermomixer is not available, the enzyme-and-sample mixture 212 can be heated at between 50° C. and 65° C. for between 25 minutes and 35 minutes and, during this period, the enzyme-and-sample mixture 212 can be mixed or shaken by removing the microcentrifuge tube 204 from the heating apparatus intermittently and shaking the microcentrifuge tube 204.

The method 200 can also comprise further heating the enzyme-and-sample mixture 212 at between 85° C. and 95° C. for between 30 seconds and 90 seconds while mixing/shaking the enzyme-and-sample mixture 212 using a thermomixer in step 200D. For example, the enzyme-and-sample mixture 212 can be heated at about 95° C. for about 60 seconds while being shaken/mixed by the thermomixer.

In alternative embodiments, the enzyme-and-sample mixture 212 can be heated at between 85° C. and 95° C. for between 30 seconds and 90 seconds without mixing/shaking the enzyme-and-sample mixture 212.

Step 200D can further comprise allowing the temperature of the enzyme-and-sample mixture 212 to equilibrate or come down to between 18° C. and 28° C.

The method 200 can also comprise briefly vortexing the enzyme-and-sample mixture 212 and then centrifuging the enzyme-and-sample mixture 212 at between 15,000×g to 17,000×g for between 30 seconds and 90 seconds in step 200E. For example, the enzyme-and-sample mixture 212 can be vortexed within the microcentrifuge tube 204 on a benchtop vortex mixer for between 15 seconds and 60 seconds and then centrifuged at approximately 16,000×g for 60 seconds.

After the centrifugation step, a supernatant 214 within the microcentrifuge tube 204 can be transferred to a clean microcentrifuge/collection tube or added directly to the bisulfite mixture 112. The supernatant 214 can be considered a digested FFPE solution.

Step 200E can further comprise transferring an aliquot of the supernatant 214 from the microcentrifuge tube 204 into another reaction vessel 216 containing the bisulfite mixture 112.

In some embodiments, the reaction vessel 216 is a reaction tube (e.g., a PCR tube) or a well of a multi-well plate pre-filled and pre-aliquoted with the bisulfite mixture 112. Transferring the aliquot of the supernatant 214 (i.e., the digested FFPE solution) into the reaction vessel 216 can comprise pipetting an aliquot of the supernatant 214 into the reaction vessel 216 containing the bisulfite mixture 112.

In one embodiment, the bisulfite mixture 112 within the reaction vessel 216 can be a frozen bisulfite mixture. For example, the temperature of the frozen bisulfite mixture can be between 0° C. and −25° C. In this embodiment, the aliquot of the supernatant 214 can be introduced directly into the reaction vessel 216 comprising the frozen bisulfite mixture 112.

In another embodiment, the bisulfite mixture 112 within the reaction vessel 216 can be a partially frozen bisulfite mixture. For example, at least part of the bisulfite mixture 112 can be frozen while the remainder of the bisulfite mixture 112 can be thawed and in liquid form. In this embodiment, the aliquot of the supernatant 214 can be introduced directly into the reaction vessel 216 comprising the partially frozen bisulfite mixture 112.

In some embodiments, a volume ratio of the supernatant 214 (i.e., the digested FFPE solution) transferred to the bisulfite mixture 112 within the reaction vessel 216 can be between 1:6 to 1:7. For example, the volume ratio of the supernatant 214 transferred to the bisulfite mixture 112 within the reaction vessel 216 can be about 1:6.5. As a more specific example, about 20 µL of the supernatant 214 can be added to about 130 µL of the bisulfite mixture 112 within the reaction vessel 216.

One unexpected discovery made by the applicant is that digested FFPE tissue sample in solution (also referred to as the digested FFPE solution) can be added directly to a frozen or partially frozen instance of the bisulfite mixture 112 disclosed herein without previously heating up the frozen or partially frozen bisulfite mixture 112 or allowing the frozen bisulfite mixture 112 to come to room temperature. The applicant discovered that the converted sequence yields obtained from a method where digested FFPE solution was added directly to a frozen or partially frozen bisulfite mixture 112 were nearly equivalent to the quantity and quality of the converted sequence yields obtained from a method where the bisulfite mixture 112 was allowed to come to room temperature prior to adding the digested FFPE solution. This means a reaction vessel 216 containing the pre-aliquoted bisulfite mixture 112 can be retrieved directly from a freezer and the digested FFPE solution can be added to the reaction vessel 216 without the lab technician or clinician having to set aside the bisulfite mixture 112 and keeping track of when the bisulfite mixture 112 was removed from the freezer. This cuts down the amount of time it takes to undertake the entire bisulfite conversion by at least 20 to 30 minutes. This time-saving step can greatly benefit clinical laboratories that process multiple FFPE samples a day.

Moreover, formulating bisulfite conversion reagents is normally a tedious and error-ridden process and the reagents must be used within a short period of time due to its instability. The present method and kits disclosed herein allows technicians or clinicians to undertake bisulfite conversion reactions without having to undertake this tedious formulation procedure. The pre-aliquoted bisulfite mixture 112 disclosed herein can be stored at between 0° C. and −25° C. and can be used immediately upon retrieval from a freezer or refrigerator. This nullifies any issues related to the instability of the reagents and saves the technician or clinician from having to repeatedly re-formulate such reagents to ensure their stability.

It is contemplated by this disclosure (and it should be understood by one of ordinary skill in the art) that, in alternative embodiments, the frozen or partially frozen bisulfite mixture 112 can be allowed to equilibrate or come to room temperature before the digested FFPE solution is added to the bisulfite mixture 112 within the reaction vessel 216.

The method can further comprise heating the reaction vessel 216 containing the digested FFPE solution and the bisulfite mixture 112 using a heating apparatus 114 at a first heating temperature between 93° C. and 98° C. (for example, between 94° C. and 96° C., or, as a more specific example, 95° C.) for a first heating period between 4 minutes and 6 minutes (for example, for 5 minutes) and then immediately lowering a temperature of the heating apparatus 114 after the first heating period to a second heating temperature between 88° C. and 92° C. (for example, between 89° C. and 91° C., or, as a more specific example, 90° C.) for a second heating period between 8 minutes and 12 minutes (for example, between 9 minutes and 11 minutes, or, as a more specific example, 10 minutes) in step 200F. For example, the reaction vessel 216 containing the digested FFPE solution and the bisulfite mixture 112 can be heated at 95° C. for 5 minutes and then the temperature can be lowered to 90° C. and the reaction vessel 216 containing the digested FFPE solution and the bisulfite mixture 112 can be heated for another 10 minutes at this new lowered heating temperature.

In some embodiments, the heating apparatus 114 can be a PCR thermal cycler. In other embodiments, the heating apparatus 114 can be a thermomixer. As a more specific example, the heating apparatus 114 can be an Eppendorf™ 5350 Thermomixer 5350 distributed by Eppendorf AG.

Step 200F can be preceded by a step where a lid of the reaction vessel 216 is closed and the reaction vessel 216 containing the digested FFPE solution and the bisulfite mixture 112 is inverted several times and centrifuged briefly. For example, the reaction vessel 216 containing the digested FFPE solution and the bisulfite mixture 112 can be inverted several times and centrifuged at between about 10,000×g to about 12,000×g for approximately 30 seconds to 90 seconds.

Step 200F can further comprise subsequently holding the reaction vessel 216 at a holding temperature between 58° C. and 62° C. (for example, at 60° C.) for a holding period between 30 seconds and 90 seconds (for example, for 60 seconds) to produce a modified sample 218. In some embodiments, step 200F can comprise subsequently holding the reaction vessel 216 at a holding temperature of 60° C. for about 60 seconds.

It has been discovered by the applicants that this unique heating process, where the reaction vessel 216 containing the digested FFPE solution and the bisulfite mixture 112 disclosed herein is heated at 95° C. for about 5 minutes, followed by heating at 90° C. for about 10 minutes, and then immediately lowering the temperature to 60° C. for about 1 minute is effective in obtaining converted DNA at concentrations (in ng/µL) substantially equivalent to and, in some cases, even higher than those produced by conventional bisulfite conversion kits in a fraction of the time. This was not expected as those of ordinary skill in the art would assume that heating the digested FFPE solution and the bisulfite mixture at such high temperatures for such a short amount of time would damage the DNA in the sample or would negatively affect the conversion reaction.

In some embodiments, the same heating apparatus 114 can be used to heat the reaction vessel 216 containing the digested FFPE solution and the bisulfite mixture 112 at the first heating temperature for the first heating period, at the second heating temperature for the second heating period, and at the holding temperature for the holding period.

Step 200F can also comprise immediately removing the reaction vessel 216 containing the modified sample 218 from the heating apparatus 114 upon completion of the holding period and briefly centrifuging the reaction vessel 216. The reaction vessel 216 containing the modified sample 218 can be removed from the heating apparatus 114 and immediately centrifuged at between about 10,000×g to about 12,000×g for approximately 30 seconds to 90 seconds. The reaction vessel 216 can be centrifuged without any further heating of the reaction vessel 216 beyond the heating period.

The modified sample 218 can then be subject to certain additional method steps 400, as depicted and described with respect to FIG. 4A, or, alternatively, additional method steps 401, as depicted and described with respect to FIG. 4B, to produce the converted DNA 432 for further downstream sequencing and analysis. The additional method steps 400 and steps 401 can comprise one or more bisulfite removal steps, desulfonation steps, and removal of the desulfonation solution. A final elution step can yield the converted DNA 432 for further downstream sequencing and analysis.

Figure 3:
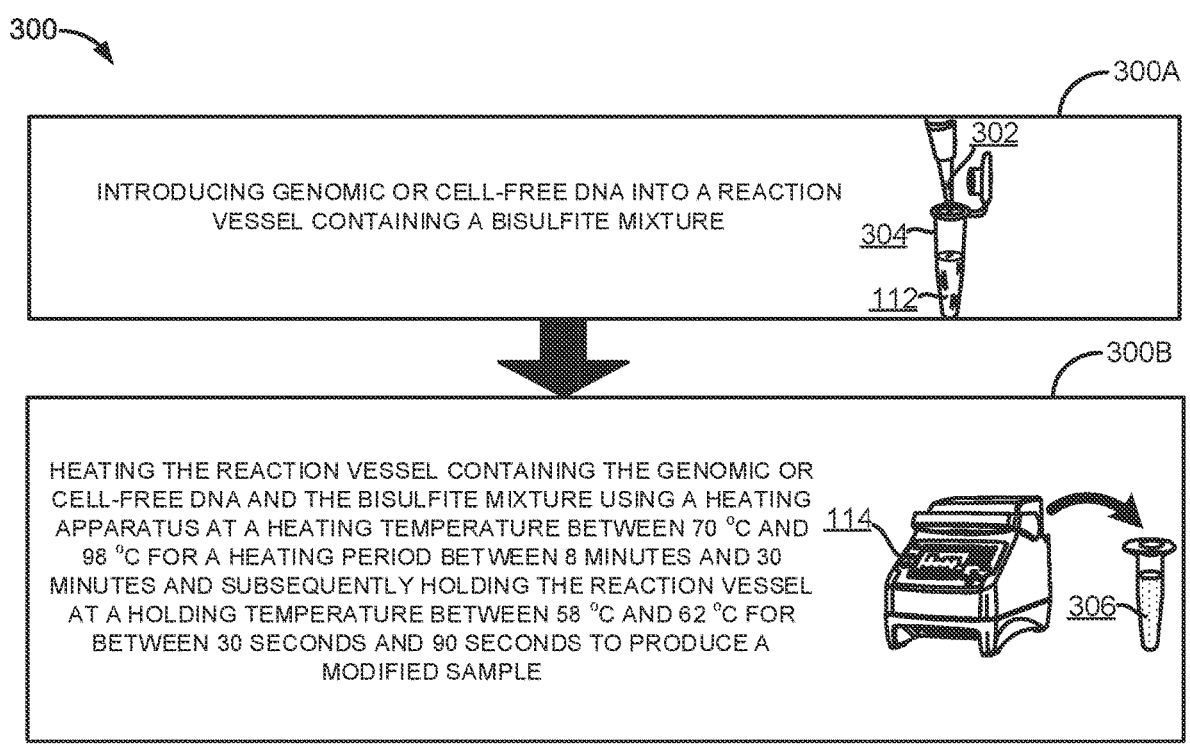
FIG. 3 illustrates one embodiment of a method of performing a bisulfite conversion using isolated or purified genomic DNA or cell-free DNA.

FIG. 3 illustrates one embodiment of a method 300 of performing a bisulfite conversion using isolated or purified genomic DNA or cell-free DNA (cfDNA). The method 300 can comprise introducing or delivering an aliquot of a solution 302 comprising the isolated/purified genomic DNA or cfDNA into a reaction vessel 304 containing the bisulfite mixture 112 in step 300A.

In some embodiments, the solution 302 can comprise the isolated/purified genomic DNA or cfDNA and a nucleic acid buffer or buffering solution.

The genomic DNA can be the chromosomal DNA of a human or animal subject. The genomic DNA can be extracted and isolated from cells, tissue, blood, or other bodily fluids of the human or animal subject. The genomic DNA can be extracted and purified using methods (typically involving one or more lysing, binding, washing, and eluting steps) and kits known in the art (e.g., a gDNA extraction kit distributed by ThermoFisher Scientific Inc.).

The cfDNA can be non-encapsulated DNA found in the bloodstream of a human or animal subject. The cfDNA can be isolated using methods and kits (e.g., the MagMAX™ cell-free DNA isolation kit distributed by ThermoFisher Scientific Inc.) known in the art. The cfDNA can include circulating tumor DNA (or ctDNA).

In some embodiments, the reaction vessel 304 is a reaction tube (e.g., a PCR tube) or a well of a multi-well plate pre-filled and pre-aliquoted with the bisulfite mixture 112. Transferring the aliquot of the solution 302 comprising the isolated/purified genomic DNA or cfDNA into the reaction vessel 304 can comprise pipetting an aliquot of the solution 302 into the reaction vessel 304 containing the bisulfite mixture 112.

In one embodiment, the bisulfite mixture 112 within the reaction vessel 304 can be a frozen bisulfite mixture. For example, the temperature of the frozen bisulfite mixture can be between 0° C. and −25° C. In this embodiment, the aliquot of the solution 302 can be introduced directly into the reaction vessel 304 comprising the frozen bisulfite mixture 112.

In another embodiment, the bisulfite mixture 112 within the reaction vessel 304 can be a partially frozen bisulfite mixture. For example, at least part of the bisulfite mixture 112 can be frozen while the remainder of the bisulfite mixture 112 can be thawed and in liquid form. In this embodiment, the aliquot of the solution 302 can be introduced directly into the reaction vessel 304 comprising the partially frozen bisulfite mixture 112.

In some embodiments, a volume ratio of the solution 302 transferred to the bisulfite mixture 112 within the reaction vessel 304 can be between 1:6 to 1:7. For example, the volume ratio of the solution 302 transferred to the bisulfite mixture 112 within the reaction vessel 304 can be about 1:6.5. As a more specific example, about 20 µL of the solution 302 can be added to about 130 µL the bisulfite mixture 112 within the reaction vessel 304.

One unexpected discovery made by the applicant is that the solution 302 comprising isolated/purified genomic DNA and cfDNA can be added directly to a frozen or partially frozen instance of the bisulfite mixture 112 disclosed herein without previously heating up the frozen or partially frozen bisulfite mixture 112 or allowing the frozen bisulfite mixture 112 to come to room temperature. The applicant discovered that the converted sequence yields obtained from a method where the solution 302 of isolated/purified genomic DNA and cfDNA was added directly to a frozen or partially frozen bisulfite mixture 112 was nearly equivalent to the quantity and quality of the converted sequence yields obtained from a method where the bisulfite mixture 112 was allowed to come to room temperature prior to adding the solution 302. This means a reaction vessel 304 containing the pre-aliquoted bisulfite mixture 112 can be retrieved directly from a freezer and the solution 302 comprising the isolated/purified genomic DNA and cfDNA can be added to the reaction vessel 304 without the lab technician or clinician having to set aside the bisulfite mixture 112 and keeping track of when the bisulfite mixture 112 was removed from the freezer. This cuts down the amount of time it takes to undertake the entire bisulfite conversion by at least 20 to 30 minutes. This time-saving step can greatly benefit clinical laboratories that process multiple DNA samples a day.

It is contemplated by this disclosure (and it should be understood by one of ordinary skill in the art) that, in alternative embodiments, the frozen or partially frozen bisulfite mixture 112 can be allowed to equilibrate or come to room temperature before the solution 302 is added to the bisulfite mixture 112 within the reaction vessel 304.

The method can further comprise heating the reaction vessel 304 containing the solution 302 and the bisulfite mixture 112 using a heating apparatus 114 at a first heating temperature between 93° C. and 98° C. (for example, between 94° C. and 96° C., or, as a more specific example, 95° C.) for a first heating period between 4 minutes and 6 minutes (for example, for 5 minutes) and then immediately lowering a temperature of the heating apparatus 114 after the first heating period to a second heating temperature between 88° C. and 92° C. (for example, between 89° C. and 91° C., or, as a more specific example, 90° C.) for a second heating period between 8 minutes and 12 minutes (for example, between 9 minutes and 11 minutes, or, as a more specific example, 10 minutes) in step 300B. For example, the reaction vessel 304 containing the solution 302 and the bisulfite mixture 112 can be heated at 95° C. for 5 minutes and then the temperature can be lowered to 90° C. and the reaction vessel 304 containing the solution 302 and the bisulfite mixture 112 can be heated for another 10 minutes at this new lowered heating temperature.

In some embodiments, the heating apparatus 114 can be a PCR thermal cycler. In other embodiments, the heating apparatus 114 can be a thermomixer. As a more specific example, the heating apparatus 114 can be an Eppendorf™ 5350 Thermomixer 5350 distributed by Eppendorf AG.

Step 300B can be preceded by a step where a lid of the reaction vessel 304 is closed and the reaction vessel 304 containing the solution 302 and the bisulfite mixture 112 is inverted several times and centrifuged briefly. For example, the reaction vessel 304 containing the solution 302 and the bisulfite mixture 112 can be inverted several times and immediately centrifuged at between about 10,000×g to about 12,000×g for approximately 30 seconds to 90 seconds.

Step 300B can further comprise subsequently holding the reaction vessel 304 at a holding temperature between 58° C. and 62° C. (for example, at 60° C.) for a holding period between 30 seconds and 90 seconds (for example, for 60 seconds) to produce a modified sample 306. In some embodiments, step 300B can comprise subsequently holding the reaction vessel 304 at a holding temperature of 60° C. for about 60 seconds.

It has been discovered by the applicants that this unique heating process, where the reaction vessel 304 containing the solution 302 and the bisulfite mixture 112 disclosed herein is heated at 95° C. for about 5 minutes, followed by heating at 90° C. for about 10 minutes, and then immediately lowering the temperature to 60° C. for about 1 minute is effective in obtaining converted DNA at concentrations (in ng/μL) substantially equivalent to and, in some cases, even higher than those produced by conventional bisulfite conversion kits in a fraction of the time. This was not expected as those of ordinary skill in the art would assume that heating the isolated/purified genomic DNA and cfDNA and the bisulfite mixture at such high temperatures for such a short amount of time would damage the DNA in the sample or would negatively affect the conversion reaction.

In some embodiments, the same heating apparatus 114 can be used to heat the reaction vessel 304 containing the solution 302 and the bisulfite mixture at the first heating temperature for the first heating period, at the second heating temperature for the second heating period, and at the holding temperature for the holding period.

Step 300B can also comprise immediately removing the reaction vessel 304 containing the modified sample 306 from the heating apparatus 114 upon completion of the holding period and briefly centrifuging the reaction vessel 304. For example, the reaction vessel 304 containing the modified sample 306 can be removed from the heating apparatus 114 upon completion of the holding period and immediately centrifuged at between about 10,000×g to about 12,000×g for approximately 30 seconds to 90 seconds. The reaction vessel 304 can be centrifuged without any further heating of the reaction vessel 304 beyond the heating period.

The modified sample 306 can then be subject to certain additional method steps 400, as depicted and described with respect to FIG. 4A, or, alternatively, additional method steps 401, as depicted and described with respect to FIG. 4B, to produce the converted DNA 432 for further downstream sequencing and analysis. The additional method steps 400 and steps 401 can comprise one or more bisulfite removal steps, desulfonation steps, and removal of the desulfonation solution. A final elution step can yield the converted DNA 432 for further downstream sequencing and analysis.

FIG. 4A illustrates additional method steps 400 for processing a modified sample 402 (for purposes of this disclosure, the modified sample 402 can refer to any one of the modified sample 116, the modified sample 218, or the modified sample 306) for producing converted DNA 432 for further downstream sequencing and analysis. The additional method steps 400 can comprise one or more bisulfite removal steps, desulfonation steps, and removal of the desulfonation solution. A final elution step can yield the converted DNA 432 for further downstream sequencing and analysis.

The additional method steps 400 can comprise introducing the modified sample 402 from the reaction vessel (e.g., any of the reaction vessel 110, the reaction vessel 216, or the reaction vessel 304) into yet another reaction vessel such as a microcentrifuge tube 404 containing a binding buffer 406 to produce a binding buffer-and-modified sample solution 408 in step 400A. If there is any crystallized or precipitated residue left over in the reaction vessel, some of the binding buffer 406 can be used to rinse out the reaction vessel and transfer the rinsed-out contents to the new microcentrifuge tube 404.

In some embodiments, the microcentrifuge tube 404 can be a 1.5 mL microcentrifuge tube. In these and other embodiments, the amount of binding buffer 406 within the microcentrifuge tube 404 can be between 500 μL to 700 μL (e.g., about 600 μL).

The binding buffer 406 can be a guanidine hydrochloride solution. For example, the binding buffer 406 can be a 5 M or 6 M guanidine hydrochloride solution.

The additional method steps 400 can also comprise closing a lid of the microcentrifuge tube 404 and inverting the microcentrifuge tube 404 at least ten times in step 400B. In some embodiments, the microcentrifuge tube 404 can be inverted between ten and 20 times. Step 400B can also comprise the additional step of centrifuging the microcentrifuge tube 404 at between about 10,000×g to about 12,000×g for approximately 30 seconds to 90 seconds.

The additional method steps 400 can further comprise transferring the binding buffer-and-modified sample solution 408 to a mini adsorption column 410 (e.g., a QIAprep® Spin Miniprep column) positioned within a first collection tube 412 in step 400C. In some embodiments, the mini adsorption column 410 can comprise a silica membrane designed to bind DNA in the presence of a chaotropic salt. For example, the mini adsorption column 410 can be a QIAprep® Spin Miniprep column distributed by QIAGEN GmbH.

Step 400C can also comprise centrifuging the first collection tube 412 containing the mini adsorption column 410 and discarding a filtrate 414 collected within the first collection tube 412 and placing the mini adsorption column 410 back into the first collection tube 412. In some embodiments, the first collection tube 412 containing the mini adsorption column 410 can be centrifuged at between 10,000×g to 15,000×g for between about 30 seconds and 90 seconds. For example, the first collection tube 412 containing the mini adsorption column 410 can be centrifuged at approximately 12,000×g for 60 seconds.

The additional method steps 400 can further comprise adding a wash buffer solution 416 to the mini adsorption column 410 and centrifuging the first collection tube 412 containing the mini adsorption column 410 in step 400D. Step 400D can further comprise discarding a filtrate 418 collected within the first collection tube 412 and placing the mini adsorption column 410 back into the first collection tube 412.

In some embodiments, the wash buffer solution 416 can be a 10 mM solution of tris(hydroxymethyl)aminomethane (Tris)-hydrochloric acid (HCl) in 80% (v/v) ethanol. The wash buffer solution 416 can have a pH of about 7.0. In these and other embodiments, between 400 μL and 600 μL of the wash buffer solution 416 can be added to the mini adsorption column 410. For example, approximately 500 μL of the wash buffer solution 416 can be added to the mini adsorption column 410.

The first collection tube 412 containing the mini adsorption column 410 can be centrifuged at between 10,000×g to 15,000×g for between about 30 seconds and 90 seconds. For example, the first collection tube 412 containing the mini adsorption column 410 can be centrifuged at approximately 12,000×g for 60 seconds.

The additional method steps 400 can also comprise adding a desulphonation mixture 420 to the mini adsorption column 410 within the first collection tube 412 and allowing the mini adsorption column 410 to remain undisturbed at a temperature between 18° C. and 28° C. (or room temperature) for between 10 minutes and 20 minutes (e.g., about 15 minutes) in step 400E.

In some embodiments, the desulphonation mixture 420 can be a solution comprising sodium hydroxide (NaOH) in 90% (v/v) ethanol. In these embodiments, the concentration of the NaOH can be between 0.2 M and 0.4 M (e.g., about 0.3 M). In these and other embodiments, between 400 µL and 600 µL of the desulphonation mixture 420 can be added to the mini adsorption column 410. For example, approximately 500 µL of the desulphonation mixture 420 can be added to the mini adsorption column 410.

The additional method steps 400 can further comprise centrifuging the first collection tube 412 containing the mini adsorption column 410 and discarding a filtrate 422 collected within the first collection tube 412 and placing the mini adsorption column 410 back into the first collection tube 412 in step 400F.

The first collection tube 412 containing the mini adsorption column 410 can be centrifuged at between 10,000×g to 15,000×g for between about 30 seconds and 90 seconds. For example, the first collection tube 412 containing the mini adsorption column 410 can be centrifuged at approximately 12,000×g for 60 seconds.

The additional method steps 400 can further comprise adding additional instances of the wash buffer solution 416 to the mini adsorption column 410 and centrifuging the first collection tube 412 containing the mini adsorption column 410 and discarding a filtrate 424 collected within the first collection tube 412 and placing the mini adsorption column 410 back into the first collection tube 412 in step 400G.

Between 400 µL and 600 µL of the wash buffer solution 416 can be added to the mini adsorption column 410. For example, approximately 500 µL of the wash buffer solution 416 can be added to the mini adsorption column 410.

The first collection tube 412 containing the mini adsorption column 410 can be centrifuged at between 10,000×g to 15,000×g for between about 30 seconds and 90 seconds. For example, the first collection tube 412 containing the mini adsorption column 410 can be centrifuged at approximately 12,000×g for 60 seconds.

The additional method steps 400 can also comprise repeating the wash step by adding further instances of the wash buffer solution 416 to the mini adsorption column 410 and centrifuging the first collection tube 412 containing the mini adsorption column 410 and discarding a filtrate 426 collected within the first collection tube 412 in step 400H.

Between 400 µL and 600 µL of the wash buffer solution 416 can be added to the mini adsorption column 410. For example, approximately 500 µL of the wash buffer solution 416 can be added to the mini adsorption column 410.

The first collection tube 412 containing the mini adsorption column 410 can be centrifuged at between 10,000×g to 15,000×g for between about 60 seconds and 180 seconds. For example, the first collection tube 412 containing the mini adsorption column 410 can be centrifuged at approximately 12,000×g for 120 seconds.

The additional method steps 400 can further comprise placing the mini adsorption column 410 into a second collection tube 428 and allowing the mini adsorption column to dry at a temperature between 18° C. and 28° C. (or room temperature) for between 1 minute and 5 minutes in step 400I. In some embodiments, the second collection tube 428 can be a new 1.5 mL microcentrifuge tube.

The additional method steps 400 can also comprise adding an elution buffer 430 to a center of the mini adsorption column 410 within the second collection tube 428 and allowing the mini adsorption column 410 to remain at a temperature between 18° C. and 28° C. for between 1 minute and 5 minutes in step 400J. For example, about 20 µL of the elution buffer 430 can be added to the center of the mini adsorption column 410 within the second collection tube 428.

In some embodiments, the elution buffer 430 can be a 1× Tris-ethylenediaminetetraacetic acid (Tris-EDTA or TE) buffer. The elution buffer 430 can have a pH of between 7 and 8. In other embodiments, the elution buffer 430 can be deionized water.

The additional method steps 400 can further comprise centrifuging the second collection tube 428 containing the mini adsorption column 410 and discarding the mini adsorption column 410 in step 400K. The filtrate collected within the second collection tube 428 can comprise bisulfite converted DNA 432 for further DNA methylation analysis.

The second collection tube 428 can be centrifuged at between 10,000×g to 15,000×g for between about 60 seconds and 180 seconds. For example, the second collection tube 428 containing the mini adsorption column 410 can be centrifuged at approximately 12,000×g for 120 seconds.

The bisulfite converted DNA 432 can be stored at between −15° C. and −25° C. For example, the bisulfite converted DNA 432 can be stored at approximately −20° C. For long-term storage, the bisulfite converted DNA 432 can be stored at between −65° C. and −75° C. (e.g., at approximately −70° C.).

FIG. 4B illustrates alternative additional method steps 401 for processing a modified sample 402 (for purposes of this disclosure, the modified sample 402 can refer to any one of the modified sample 116, the modified sample 218, or the modified sample 306) for producing converted DNA 432 for further downstream sequencing and analysis. The additional method steps 401 can comprise introducing the modified sample 402 from the reaction vessel (e.g., any of the reaction vessel 110, the reaction vessel 216, or the reaction vessel 304) into yet another reaction vessel such as microcentrifuge tube 403 containing a binding buffer 406 and a carboxylated paramagnetic bead solution 405 in step 401A.

In some embodiments, the microcentrifuge tube 403 can be a 1.5 mL microcentrifuge tube. In these and other embodiments, the amount of binding buffer 406 within the microcentrifuge tube 403 can be between 300 µL to 500 µL (e.g., about 400 µL).

The binding buffer 406 can be a guanidine hydrochloride solution. For example, the binding buffer 406 can be a 5 M or 6 M guanidine hydrochloride solution.

The amount of carboxylated paramagnetic bead solution 405 within the microcentrifuge tube 403 can be between approximately 1.5 µL and 3.0 µL (e.g., about 2 µL). The carboxylated paramagnetic bead solution 405 can comprise carboxylated paramagnetic beads 407 in solution with a crowding agent such as polyethylene glycol (PEG) and a salt (e.g., sodium chloride). The carboxylated paramagnetic beads 407 can also be referred to as solid phase reversible immobilization (SPRI) beads. The carboxylated paramagnetic beads 407 can be made of a polystyrene core surrounded by a layer of magnetite and coated with carboxyl-functional groups that are configured to reversibly bind to DNA. In some embodiments, the carboxylated paramagnetic beads 407 can be AMPure® beads distributed by Beckman Coulter, Inc.

The carboxyl-functional groups on the paramagnetic beads 407 reversibly bind to DNA within the modified sample 402 in the presence of the crowding agent and salt.

Step 401A can also comprise vortexing the microcentrifuge tube 403 using a benchtop vortex mixer or shaker. The microcentrifuge tube 403 can be vortexed between 10 seconds and 30 seconds (e.g., 20 seconds). After the microcentrifuge tube 403 is vortexed, the microcentrifuge tube 403 containing the modified sample 402, the binding buffer 406, and the carboxylated paramagnetic bead solution 405 can be allowed to remain undisturbed at a temperature between 18° C. and 28° C. (or room temperature) for between 3 minutes and 7 minutes (e.g., about 5 minutes).

The additional method steps 401 can also comprise centrifuging the microcentrifuge tube 403 at between about 10,000×g to about 12,000×g for approximately 30 seconds to 90 seconds in step 401B. In some embodiments, the microcentrifuge tube 403 can be centrifuged using a benchtop laboratory centrifuge. When the reaction vessel is a well of a multi-well or microtiter plate, the multi-well plate or microtiter plate, the entire plate can be centrifuged using a microplate centrifuge.

The additional method steps 401 can also comprise placing the microcentrifuge tube 403 in proximity to a magnet 409 for between 3 minutes and 7 minutes in step 401C. In some embodiments, the magnet 409 can refer to a magnet of a magnetic separation rack or platform. For example, the magnetic separation rack can comprise a plurality of wells with at least one magnet positioned at the bottom of each well. For example, the magnetic separation rack can be a DynaMag® magnetic rack. In other embodiments, the magnetic separation rack can be any type of magnetic rack or platform comprising one or more magnets positioned on the bottom or sides of the rack or platform. The magnets of the magnetic separation rack can aggregate and collect the carboxylated paramagnetic beads 407 including any carboxylated paramagnetic beads 407 with DNA bound to such beads.

Step 401C can also comprise removing and discarding a supernatant 411 from the microcentrifuge tube 403 while the carboxylated paramagnetic beads 407 (along with DNA bound to such beads) are immobilized to an inner surface of the microcentrifuge tube 403 by the magnet 409. Removing and discarding the supernatant 411 can comprise using a micropipette to aspirate the supernatant 411 from the microcentrifuge tube 403 into the pipette tip and expelling the supernatant 411 to discard the supernatant 411.

The additional method steps 401 can further comprise adding a wash buffer solution 416 to the microcentrifuge tube 403 in step 401D. In some embodiments, the wash buffer solution 416 can be a 10 mM solution of tris(hydroxymethyl)aminomethane (Tris)-hydrochloric acid (HCl) in 80% (v/v) ethanol. The wash buffer solution 416 can have a pH of about 7.0. In these and other embodiments, between 80 µL and 120 µL of the wash buffer solution 416 can be added to the microcentrifuge tube 403. For example, approximately 100 µL of the wash buffer solution 416 can be added to the microcentrifuge tube 403.

Step 401D can further comprise vortexing the microcentrifuge tube 403 containing the wash buffer solution 416 and the DNA-bound carboxylated paramagnetic beads 407 using a benchtop vortex mixer or shaker. The microcentrifuge tube 403 can be vortexed between 10 seconds and 30 seconds (e.g., 20 seconds). Step 401D can also comprise centrifuging the microcentrifuge tube 403 at between 10,000×g to 15,000×g for between about 30 seconds and 90 seconds. For example, the microcentrifuge tube 403 can be centrifuged at approximately 12,000×g for 60 seconds.

The additional method steps 401 can also comprise placing the microcentrifuge tube 403 in proximity, once again, to the magnet 409 for between 1 minute and 3 minutes in step 401E. Step 401E can also comprise removing and discarding a supernatant 413 from the microcentrifuge tube 403 while the carboxylated paramagnetic beads 407 (along with DNA bound to such beads) are immobilized to an inner surface of the microcentrifuge tube 403 by the magnet 409. Removing and discarding the supernatant 413 can comprise using a micropipette to aspirate the supernatant 413 from the microcentrifuge tube 403 into the pipette tip and expelling the supernatant 413 to discard the supernatant 413.

The additional method steps 401 can also comprise adding a desulphonation mixture 420 to the microcentrifuge tube 403 and allowing the microcentrifuge tube 403 to remain at a temperature between 18° C. and 28° C. (or room temperature) for a period of time between 10 minutes and 20 minutes (e.g., about 15 minutes) in step 401F. In some embodiments, the microcentrifuge tube 403 can be inverted every 3 minutes to 5 minutes during this period of time (e.g., during this 10-20 minutes period) with the lid of the microcentrifuge tube 403 closed to keep the carboxylated paramagnetic beads 407 in suspension. In certain embodiments, the microcentrifuge tube 403 can be inverted at least two times during this period of time. Step 401F can also comprise vortexing the microcentrifuge tube 403 for between 10 seconds and 30 seconds (e.g., 20 seconds) prior to allowing the microcentrifuge tube 403 to remain at room temperature during this 10 to 20 minutes period of time.

In some embodiments, the desulphonation mixture 420 can be a solution comprising sodium hydroxide (NaOH) in 90% (v/v) ethanol. In these embodiments, the concentration of the NaOH can be between 0.2 M and 0.4 M (e.g., about 0.3 M). In these and other embodiments, between 80 µL and 120 µL of the desulphonation mixture 420 can be added to the microcentrifuge tube 403 as part of step 401F. For example, approximately 100 µL of the desulphonation mixture 420 can be added to the microcentrifuge tube 403.

The additional method steps 401 can also comprise centrifuging the microcentrifuge tube 403 at between about 10,000×g to about 12,000×g for approximately 30 seconds to 90 seconds in step 401G. In some embodiments, the microcentrifuge tube 403 can be centrifuged using a benchtop laboratory centrifuge. When the reaction vessel is a well of a multi-well or microtiter plate, the multi-well plate or microtiter plate, the entire plate can be centrifuged using a microplate centrifuge.

The additional method steps 401 can also comprise placing the microcentrifuge tube 403, once again, in proximity to the magnet 409 for between 1 minute and 3 minutes in step 401G. For example, the microcentrifuge tube 403 can be placed on a magnetic separation rack for approximately 2 minutes. Step 401G can also comprise removing and discarding a supernatant 415 from the microcentrifuge tube 403 while the carboxylated paramagnetic beads 407 (along with DNA bound to such beads) are immobilized to an inner surface of the microcentrifuge tube 403 by the magnet 409. Removing and discarding the supernatant 415 can comprise using a micropipette to aspirate the supernatant 415 from the microcentrifuge tube 403 into the pipette tip and expelling the supernatant 415 to discard the supernatant 415.

The additional method steps 401 can further comprise adding additional instances of the wash buffer solution 416 to the microcentrifuge tube 403 in step 401H. Between 80 µL and 120 µL of the wash buffer solution 416 can be added to the microcentrifuge tube 403. For example, approximately 100 µL of the wash buffer solution 416 can be added to the microcentrifuge tube 403. Step 401H can further comprise vortexing the microcentrifuge tube 403 containing the wash buffer solution 416 and the DNA-bound carboxylated paramagnetic beads 407 using a benchtop vortex mixer or shaker. The microcentrifuge tube 403 can be vortexed between 10 seconds and 30 seconds (e.g., 20 seconds). Step 401H can also comprise centrifuging the microcentrifuge tube 403 at between 10,000×g to 15,000×g for between about 30 seconds and 90 seconds. For example, the microcentrifuge tube 403 can be centrifuged at approximately 12,000×g for 60 seconds.

Step 401H can also comprise placing the microcentrifuge tube 403 in proximity, once again, to the magnet 409 for between 1 minute and 3 minutes in step 401H. Step 401H can also comprise removing and discarding a supernatant 417 formed within the microcentrifuge tube 403 while the carboxylated paramagnetic beads 407 (along with DNA bound to such beads) are immobilized to an inner surface of the microcentrifuge tube 403 by the magnet 409. Removing and discarding the supernatant 417 can comprise using a micropipette to aspirate the supernatant 417 from the microcentrifuge tube 403 into the pipette tip and expelling the supernatant 417 to discard the supernatant 417.

In some embodiments, the additional method steps 401 can comprise repeating step 401H one more time. This can include adding additional instances of the wash buffer solution 416 (e.g., 100 µL of the wash buffer solution 416) to the microcentrifuge tube 403, vortexing and centrifuging the microcentrifuge tube 403, and removing and discarding the supernatant 417 formed within the microcentrifuge tube 403 while the microcentrifuge tube 403 is placed in proximity to the magnet 409 (e.g., on a magnetic separation rack).

The additional method steps 401 can also comprise removing any traces of the wash buffer solution 416 from a bottom of the microcentrifuge tube 403 (for example, by aspirating using a 20 µL micropipette) and allowing the DNA-bound carboxylated paramagnetic beads 407 to dry in open air at room temperature (e.g., between 18° C. and 28° C.) for between 3 minutes and 7 minutes (e.g., 5 minutes) in step 401I.

The additional method steps 401 can also comprise adding an elution buffer 430 to the microcentrifuge tube 403 and vortexing the microcentrifuge tube 403 for between 10 seconds and 30 seconds (e.g., 20 seconds) in step 401J. Step 401J can also comprise allowing the microcentrifuge tube 403 to remain at a temperature between 18° C. and 28° C. (or room temperature) for a period of time between 3 minutes and 8 minutes (e.g., about 5 minutes).

The additional method steps 401 can further comprise centrifuging the microcentrifuge tube 403 at between 10,000×g to 15,000×g for between about 30 seconds and 90 seconds in step 401K. For example, the microcentrifuge tube 403 can be centrifuged at approximately 12,000×g for 60 seconds.

Step 401K can also comprise placing the microcentrifuge tube 403 in proximity, once again, to the magnet 409 for between 1 minute and 3 minutes. Step 401K can further comprise removing a supernatant from the microcentrifuge tube 403 while only the carboxylated paramagnetic beads 407 are immobilized to an inner surface of the microcentrifuge tube 403 by the magnet 409 (e.g., placing the microcentrifuge tube 403 on a magnetic separation rack).

The supernatant, at this step, comprises the bisulfite converted DNA 432. Removing the supernatant comprising the bisulfite converted DNA 432 can be done using a micropipette to aspirate the supernatant from the microcentrifuge tube 403 and transferring the supernatant to a clean reaction vessel, tube, or well.

The bisulfite converted DNA 432 can be stored at between −15° C. and −25° C. For example, the bisulfite converted DNA 432 can be stored at approximately −20° C. For long-term storage, the bisulfite converted DNA 432 can be stored at between −65° C. and −75° C. (e.g., at approximately −70° C.).

One advantage of the additional method steps 401 disclosed herein is that such steps can be easily automated on a nucleic acid extraction machine which can lead to even greater time-savings Bisulfite Conversion Kit Disclosed is also a bisulfite conversion kit or a reagent kit for performing bisulfite conversion of DNA for downstream DNA methylation analysis. The kit can comprise the bisulfite mixture 112, the binding buffer 406, the wash buffer solution 416, the desulphonation mixture 420, and the elution buffer 430.

In some embodiments, the kit can also comprise the nucleic acid buffer 206 and the digestion enzyme mixture 210.

As previously discussed, the bisulfite mixture 112 can comprise ammonium bisulfite, ammonium sulfite, sodium bisulfite, and deionized water (see Table 1). The bisulfite mixture 112 can be pre-aliquoted into reaction vessels or tubes (e.g., about 130 µL of the bisulfite mixture 112 can be pre-aliquoted into each reaction vessel or tube) and kept frozen or partially frozen.

The binding buffer 406 can be a guanidine hydrochloride solution. The wash buffer solution 416 can be a solution of Tris-HCl in 80% (v/v) ethanol. The wash buffer solution 416 can have a pH of about 7.0. The desulphonation mixture 420 can be a solution comprising NaOH in 90% (v/v) ethanol. The elution buffer 430 can be a 1×TE buffer.

The nucleic acid buffer 206 can comprise a Tris-HCl solution, NaCl, EDTA, and SDS (see Table 2). The digestion enzyme mixture 210 can be a solution comprising proteinase K.

Presented in Table 3 below is an example reagent kit for performing bisulfite conversion of DNA:

TABLE 1

Example Bisulfite Conversion Kit

| Kit Components | Composition |
| --- | --- |
| Bisulfite Mixture | 10M mixture with ammonium bisulfite, sodium bisulfite, ammonium sulfite, and DI water |
| Binding Buffer | 6M guanidine hydrochloride solution |
| Wash Buffer Solution | 10 mM Tris-HCl 80% (v/v) ethanol, pH 7.0 |
| Desulphonation Mixture | 0.3M NaOH in 90% (v/v) ethanol |
| Elution Buffer | 1X TE buffer |
| Nucleic Acid Buffer | 100 mM Tris-HCl (pH 7.5), 200 mM NaCl, 2 mM EDTA, and 1% SDS |
| Digestion Enzyme Mixture | Proteinase K |

Figure 5:
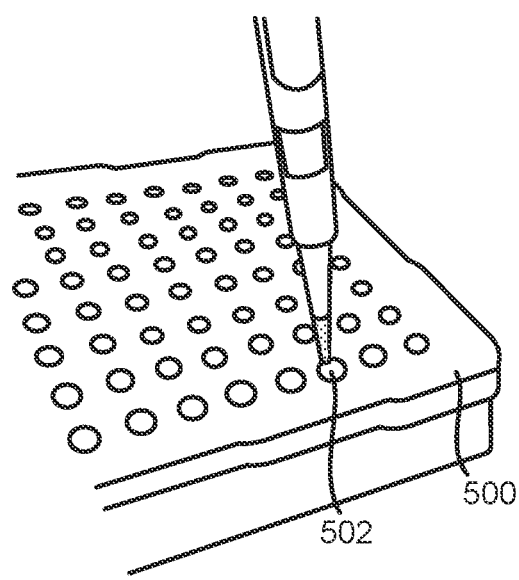
FIG. 5 illustrates a multi-well plate comprising a plurality of reaction wells that can each be pre-aliquoted with a bisulfite mixture.

FIG. 5 illustrates a multi-well plate 500 or microtiter plate comprising a plurality of reaction wells 502. In some embodiments, the multi-well plate 500 can be a 48-well plate or a 96-well plate. For purposes of this disclosure, any references to a reaction vessel (e.g., any of the microcentrifuge tubes or any of the reaction vessel 110, the reaction vessel 216, or the reaction vessel 304) can also refer to each of the reaction wells 502 of the multi-well plate 500.

For example, each of the reaction wells 502 of the multi-well plate 500 can be pre-aliquoted with the bisulfite mixture 112 and biological samples (e.g., the re-suspended urine-derived cellular debris, the digested FFPE solution, or the solution containing the isolated/purified DNA sample) can be introduced directly into each reaction well 502 of the multi-well plate 500. The entire multi-well plate 500 can then be heated in a heating apparatus such as a PCR thermal cycler.

The entire multi-well plate 500 can also be centrifuged or spun down using a microplate centrifuge. The entire multi-well plate 500 can also be vortexed using a microplate vortex mixer.

FIG. 6A is a table comparing the performance of the presently disclosed bisulfite conversion kit and method with two conventional bisulfite conversion kits and their associated protocols as it relates to the quantity and purity of the converted DNA. The two conventional bisulfite conversion kits are the widely-used EpiMark® bisulfite conversion kit distributed by New England Biolabs, Inc. and the BisulFlash™ DNA modification kit distributed by EpiGentek Group Inc. With respect to these conversions, the starting material was a slide-mounted FFPE of human lung tissue showing signs of non-small cell lung cancer.

DNA concentration was measured using fluorescence assays conducted by a fluorometer (e.g., Qubit® fluorometer) optimized for certain target-specific fluorescent dyes (e.g., Qubit® fluorescent dyes) and DNA quantity was measured using SYBR Green quantitative real-time PCR (qPCR). SYBR Green qPCR was conducted using a commercially-available SYBR Green PCT kit such as the QuantiTect® SYBR Green PCT kit distributed by QIAGEN GmbH. For the SYBR Green qPCR assays, part of the human glyceraldehyde 3-phosphate dehydrogenase (GAPDH) gene, a commonly used housekeeping gene, was used as the target sequence.

DNA purity was measured using ultraviolet (UV) spectrophotometric analysis. More specifically, DNA purity was measured using the ratio of the absorbance of the converted DNA at 260 nm versus 280 nm (A260/A280). Sufficiently pure DNA has an A260/A280 ratio of greater than 1.8.

As shown in the table in FIG. 6A, the bisulfite conversion kit and conversion method disclosed herein produced converted DNA at concentrations (in ng/µL) substantially equivalent to and, in some cases, even higher than those produced by the two conventional bisulfite conversion kits. Moreover, the cycle threshold (or Ct) values obtained from the SYBR Green qPCR measurements were also closely aligned with Ct values obtained from similar qPCR runs conducted on DNA converted using the two conventional bisulfite conversion kits (where any differences were within expected error ranges).

FIG. 6B is another table comparing the performance of the presently disclosed bisulfite conversion kit and method with the same two conventional bisulfite conversion kits (the EpiMark® bisulfite conversion kit and the BisulFlash™ DNA modification kit) and their associated protocols as it relates to the quantity and purity of the converted DNA. With respect to these conversions, the starting material was a human urine sample directly introduced into the bisulfite mixture (see, e.g., FIG. 1).

DNA concentration (in ng/µL) was measured using fluorescence assays conducted by the Qubit® fluorometer optimized for Qubit® fluorescent dyes, DNA purity was measured using A260/A280, and DNA quantity was measured using SYBR Green qPCR with the GAPDH gene as the target sequence.

As shown in the table in FIG. 6B, the bisulfite conversion kit and conversion method disclosed herein produced converted DNA at concentrations substantially equivalent to and, in some cases, even higher than those produced by the two conventional bisulfite conversion kits. Moreover, the Ct values obtained from the SYBR Green qPCR measurements were also closely aligned with Ct values obtained from similar qPCR runs conducted on DNA converted using the two conventional bisulfite conversion kits (where any differences were within expected error ranges).

FIG. 6C is yet another table comparing the performance of the presently disclosed bisulfite conversion kit and method with the same two conventional bisulfite conversion kits (the EpiMark® bisulfate conversion kit and the BisulFlash™ DNA modification kit) and their associated protocols as it relates to the quantity and purity of the converted DNA. With respect to these conversions, the starting material included cfDNA, such as ctDNA, from two different patients.

DNA concentration (in ng/µL) was measured using fluorescence assays conducted by the Qubit® fluorometer optimized for Qubit® fluorescent dyes and DNA quantity was measured using SYBR Green qPCR with the GAPDH gene as the target sequence.

As shown in the table in FIG. 6C, the bisulfite conversion kit and conversion method disclosed herein produced converted DNA at concentrations substantially equivalent to those produced by the two conventional bisulfite conversion kits. Moreover, the Ct values obtained from the SYBR Green qPCR measurements were also closely aligned with Ct values obtained from similar qPCR runs conducted on DNA converted using the two conventional bisulfite conversion kits (where any differences were within expected error ranges).

FIG. 7 is a table showing the results of methylation assays conducted using SYBR Green qPCR with the GAPDH gene as the target sequence. Primers were designed specifically for both the unconverted (or precursor) DNA and the bisulfite converted DNA. DNA concentrations (in ng/µL), for both the bisulfite converted and unconverted DNA, were also measured using fluorescence assays conducted by the Qubit® fluorometer optimized for Qubit® fluorescent dyes.

As shown in the table in FIG. 7, when the sample contained unconverted DNA, the Ct values obtained from the SYBR Green qPCR assays conducted using primers designed for such unconverted DNA showed strong positive reactions (i.e., Ct<29). Similarly, the Ct values obtained from the SYBR Green qPCR assays conducted using primers designed for such unconverted DNA showed predictably weak reactions (i.e., Ct>38) since Ct values are inversely proportional to the amount of target nucleic acid in the sample.

Moreover, the table in FIG. 7 showed that when the sample contained bisulfite converted DNA, the Ct values obtained from the SYBR Green qPCR assays conducted using primers designed for such converted DNA showed strong positive reactions (i.e., Ct<29). Similarly, the Ct values obtained from the SYBR Green qPCR assays conducted using primers designed for unconverted DNA showed predictably weak reactions (i.e., Ct>38).

Figure 8:
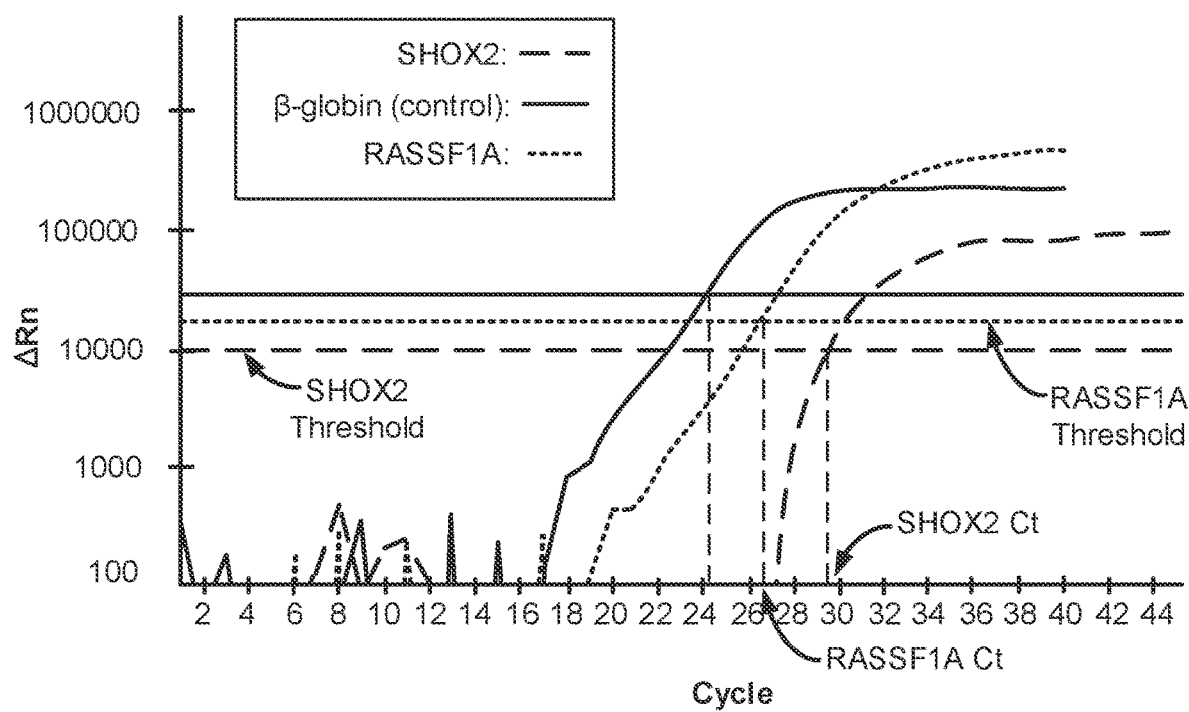
FIG. 8 is a real-time amplification plot showing the results of a SYBR Green qPCR amplification reaction to determine the methylation status of the SHOX2 and the RASSF1A genes in a slide-mounted FFPE of human lung tissue from a patient showing signs of lung cancer.

FIG. 8 is a real-time amplification plot showing the results of a SYBR Green qPCR amplification reaction to determine the methylation status of the short stature homeobox gene two (SHOX2) and the RAS association domain family 1, isoform A (RASSF1A) genes in a slide-mounted FFPE of human lung tissue from a patient showing signs of lung cancer. The SHOX2 and RASSF1A genes are known for their diagnostic and prognostic value in lung cancer pathology (see Ren et al. "Methylation analysis of SHOX2 and RASSF1A in bronchoalveolar lavage fluid for early lung cancer diagnosis." *Ann Diagn Pathol* 27 (2017): 57-61; Shi et al. "Performance Evaluation of SHOX2 and RASSF1A Methylation for the Aid in Diagnosis of Lung Cancer Based on the Analysis of FFPE Specimen." *Frontiers in Oncology* 10 (2020): 2768; Zhang et al. "DNA methylation analysis of the SHOX2 and RASSF1A panel in bronchoalveolar lavage fluid for lung cancer diagnosis." *Journal of Cancer* 8.17 (2017): 3585). The human hemoglobin subunit beta (β-globin or HBB) gene was used as the control.

A piece of the slide-mounted FFPE lung tissue was processed using the method 200 and bisulfite conversion kit disclosed herein. The converted DNA was subjected to the SYBR Green qPCR amplification reaction using methylation-specific primers including primers specifically designed for the bisulfite converted sequences. As shown in FIG. 8, the Ct value of the RASSF1A gene was approximately 26.7 and the Ct value of the SHOX2 gene was approximately 29.2. These Ct values indicate strong positive reactions and methylation of the SHOX2 and RASSF1A genes in cells of the lung tissue sample (where hypermethylation of the promoter regions of these two genes is often associated with lung cancer). As such, the bisulfite conversion kit and bisulfite conversion methods disclosed herein are effective in converting methylated DNA and can serve as the initial steps in a DNA methylation detection protocol for disease diagnostics.

A number of embodiments have been described. Nevertheless, it will be understood by one of ordinary skill in the art that various changes and modifications can be made to this disclosure without departing from the spirit and scope of the embodiments. Elements of systems, devices, apparatus, and methods shown with any embodiment are exemplary for the specific embodiment and can be used in combination or otherwise on other embodiments within this disclosure. For example, the steps of any methods depicted in the figures or described in this disclosure do not require the particular order or sequential order shown or described to achieve the desired results. In addition, other steps operations may be provided, or steps or operations may be eliminated or omitted from the described methods or processes to achieve the desired results. Moreover, any components or parts of any apparatus or systems described in this disclosure or depicted in the figures may be removed, eliminated, or omitted to achieve the desired results. In addition, certain components or parts of the systems, devices, or apparatus shown or described herein have been omitted for the sake of succinctness and clarity.

Accordingly, other embodiments are within the scope of the following claims and the specification and/or drawings may be regarded in an illustrative rather than a restrictive sense.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit, or scope of the present invention.

Methods recited herein may be carried out in any order of the recited events that is logically possible, as well as the recited order of events. Moreover, additional steps or operations may be provided or steps or operations may be eliminated to achieve the desired result.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein. For example, a description of a range from 1 to 5 should be considered to have disclosed subranges such as from 1 to 3, from 1 to 4, from 2 to 4, from 2 to 5, from 3 to 5, etc. as well as individual numbers within that range, for example 1.5, 2.5, etc. and any whole or partial increments therebetween.

All existing subject matter mentioned herein (e.g., publications, patents, patent applications) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

Reference to the phrase "at least one of", when such phrase modifies a plurality of items or components (or an enumerated list of items or components) means any combination of one or more of those items or components. For example, the phrase "at least one of A, B, and C" means: (i) A; (ii) B; (iii) C; (iv) A, B, and C; (v) A and B; (vi) B and C; or (vii) A and C.

In understanding the scope of the present disclosure, the term "comprising" and its derivatives, as used herein, are intended to be open-ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" "element," or "component" when used in the singular can have the dual meaning of a single part or a plurality of parts. As used herein, the following directional terms "forward, rearward, above, downward, vertical, horizontal, below, transverse, laterally, and vertically" as well as any other similar directional terms refer to those positions of a device or piece of equipment or those directions of the device or piece of equipment being translated or moved.

Finally, terms of degree such as "substantially", "about" and "approximately" as used herein mean the specified value or the specified value and a reasonable amount of deviation from the specified value (e.g., a deviation of up to ±0.1%, ±1%, ±5%, or ±10%, as such variations are appropriate) such that the end result is not significantly or materially changed. For example, "about 1.0 g" can be interpreted to mean "1.0 g" or between "0.9 g and 1.1 g." When terms of degree such as "about" or "approximately" are used to refer to numbers or values that are part of a range, the term can be used to modify both the minimum and maximum numbers or values.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure.

What is claimed is:

1. A method of performing a bisulfite conversion of deoxyribonucleic acid (DNA) from a urine sample as part of a DNA-methylation-based urinalysis, the method comprising:
   introducing an aliquot of the urine sample into a first reaction vessel, wherein the urine sample is a direct urine sample without any buffers added to the urine sample;
   centrifuging the urine sample within the first reaction vessel;
   removing at least part of a supernatant from the first reaction vessel by decanting or pipetting the supernatant out of the first reaction vessel, wherein urine-derived cellular debris from the urine sample remains at a bottom of the first reaction vessel after at least part of the supernatant is removed;
   re-suspending the urine-derived cellular debris within the first reaction vessel by vortexing or shaking the first reaction vessel;
   transferring a portion of the re-suspended urine-derived cellular debris from the first reaction vessel into a second reaction vessel containing a bisulfite mixture;
   heating the second reaction vessel containing the urine-derived cellular debris and the bisulfite mixture using a heating apparatus at a first heating temperature between 93° C. and 98° C. for a first heating period between 4 minutes and 6 minutes, immediately lowering a temperature of the heating apparatus after the first heating period to a second heating temperature between 88° C. and 92° C. for a second heating period between 8 minutes and 12 minutes, and subsequently holding the second reaction vessel at a holding temperature between 58° C. and 62° C. for a holding period between 30 seconds and 90 seconds immediately after the second heating period to produce a modified sample; and
   immediately removing the second reaction vessel containing the modified sample from the heating apparatus upon completion of the holding period and centrifuging the second reaction vessel, wherein the second reaction vessel is centrifuged without any further heating of the second reaction vessel.

2. The method of claim 1, wherein the bisulfite mixture within the second reaction vessel is a frozen bisulfite mixture, wherein a temperature of the frozen bisulfite mixture is between 0° C. and −25° C., and wherein the portion of the re-suspended urine-derived cellular debris is introduced directly into the second reaction vessel comprising the frozen bisulfite mixture.

3. The method of claim 1, wherein the bisulfite mixture within the second reaction vessel is a partially frozen bisulfite mixture, and wherein the portion of the re-suspended urine-derived cellular debris is introduced directly into the second reaction vessel comprising the partially frozen bisulfite mixture.

4. The method of claim 1, further comprising:
   introducing the modified sample from the second reaction vessel into a third reaction vessel containing a binding buffer to produce a binding buffer-and-modified sample solution;
   closing a lid of the third reaction vessel and inverting the third reaction vessel at least ten times; and
   transferring the binding buffer-and-modified sample solution to a mini adsorption column positioned within a first collection tube; and
   centrifuging the first collection tube containing the mini adsorption column and discarding a filtrate collected within the first collection tube and placing the mini adsorption column back into the first collection tube.

5. The method of claim 4, further comprising:
   adding a wash buffer solution to the mini adsorption column;
   centrifuging the first collection tube containing the mini adsorption column and discarding the filtrate collected within the first collection tube and placing the mini adsorption column back into the first collection tube;
   adding a desulphonation mixture to the mini adsorption column within the first collection tube and allowing the mini adsorption column to remain undisturbed at a temperature between 18° C. and 28° C. for between 10 minutes and 20 minutes;
   centrifuging the first collection tube containing the mini adsorption column and discarding the filtrate collected within the first collection tube and placing the mini adsorption column back into the first collection tube;
   adding additional instances of the wash buffer solution to the mini adsorption column;
   centrifuging the first collection tube containing the mini adsorption column and discarding the filtrate collected within the first collection tube and placing the mini adsorption column back into the first collection tube;
   adding further instances of the wash buffer solution to the mini adsorption column; and
   centrifuging the first collection tube containing the mini adsorption column and discarding the filtrate collected within the first collection tube.

6. The method of claim 5, further comprising:
   placing the mini adsorption column into a second collection tube and allowing the mini adsorption column to dry at a temperature between 18° C. and 28° C. for between 1 minute and 5 minutes;
   adding an elution buffer to a center of the mini adsorption column within the second collection tube and allowing the mini adsorption column to remain at a temperature between 18° C. and 28° C. for between 1 minute and 5 minutes; and
   centrifuging the second collection tube containing the mini adsorption column and discarding the mini adsorption column, wherein filtrate collected within the second collection tube comprises bisulfite converted DNA for further DNA methylation analysis.

7. The method of claim 6, wherein the binding buffer is a guanidine hydrochloride solution having a concentration of between 5 M and 6 M, and wherein the desulphonation mixture comprises sodium hydroxide in 90% (v/v) ethanol, wherein a concentration of the sodium hydroxide is between 0.2 M and 0.4 M.

8. The method of claim 1, further comprising:
introducing the modified sample from the second reaction vessel into a third reaction vessel containing a binding buffer and a carboxylated paramagnetic bead solution and centrifuging the third reaction vessel;
placing the third reaction vessel in proximity to a magnet for between 3 minutes and 8 minutes and removing and discarding a supernatant formed within the third reaction vessel;
adding a wash buffer solution to the third reaction vessel and vortexing and centrifuging the third reaction vessel;
placing the third reaction vessel in proximity to the magnet for between 1 minute and 3 minutes and removing and discarding a supernatant formed within the third reaction vessel;
adding a desulphonation mixture to the third reaction vessel and allowing the third reaction vessel to remain at a temperature between 18° C. and 28° C. for a period of time between 10 minutes and 20 minutes, wherein the third reaction vessel is inverted at least two times during this period of time with a lid of the third reaction vessel closed;
centrifuging the third reaction vessel, placing the third reaction vessel in proximity to the magnet for between 1 minute and 3 minutes, and removing and discarding a supernatant formed within the third reaction vessel;
adding additional instances of the wash buffer solution to the third reaction vessel and vortexing and centrifuging the third reaction vessel;
placing the third reaction vessel in proximity to the magnet for between 1 minute and 3 minutes and removing and discarding a supernatant formed within the third reaction vessel;
adding an elution buffer to the third reaction vessel and allowing the third reaction vessel to remain at a temperature between 18° C. and 28° C. for between 3 minutes and 8 minutes; and
centrifuging the third reaction vessel and placing the third reaction vessel in proximity to the magnet for between 1 minute and 3 minutes, wherein a supernatant formed within the third reaction vessel comprises bisulfite converted DNA for further DNA methylation analysis.

9. The method of claim 1, wherein a volume ratio of the re-suspended urine-derived cellular debris transferred to the bisulfite mixture within the second reaction vessel is between 1:6 to 1:7.

10. The method of claim 1, wherein the bisulfite mixture comprises:
ammonium bisulfite;
ammonium sulfite;
sodium bisulfite; and
deionized water.

* * * * *